(12) United States Patent
Fortson et al.

(10) Patent No.: US 12,337,133 B2
(45) Date of Patent: Jun. 24, 2025

(54) ACCESS CLOSURE DEVICE

(71) Applicant: Abbott Cardiovascular Systems, Inc., Santa Clara, CA (US)

(72) Inventors: Aaron M. Fortson, Fremont, CA (US); Stephen D. Pacetti, San Jose, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 40 days.

(21) Appl. No.: 17/524,889

(22) Filed: Nov. 12, 2021

(65) Prior Publication Data

US 2022/0152372 A1 May 19, 2022

Related U.S. Application Data

(60) Provisional application No. 63/114,214, filed on Nov. 16, 2020.

(51) Int. Cl.
*A61M 39/02* (2006.01)
*A61M 25/10* (2013.01)

(52) U.S. Cl.
CPC ..... *A61M 39/0247* (2013.01); *A61M 25/1002* (2013.01); *A61M 25/10182* (2013.11); *A61M 25/10186* (2013.11); *A61M 2025/1054* (2013.01); *A61M 2039/0258* (2013.01); *A61M 2039/0288* (2013.01); *A61M 2039/0297* (2013.01)

(58) Field of Classification Search
CPC .. A61M 2025/1054; A61M 2039/0258; A61M 2039/0288; A61M 2039/0297; A61M 25/1002; A61M 25/10182; A61M 25/10186; A61M 39/0247
See application file for complete search history.

(56) References Cited

U.S. PATENT DOCUMENTS

| | | | |
|---|---|---|---|
| 4,364,392 A * | 12/1982 | Strother | A61B 17/0057 606/195 |
| 4,517,979 A * | 5/1985 | Pecenka | A61B 17/12136 604/97.02 |
| 6,063,085 A * | 5/2000 | Tay | A61B 17/0057 606/50 |
| 6,638,292 B2 | 10/2003 | Adams | |
| 6,736,793 B2 | 5/2004 | Meyer et al. | |
| 7,975,697 B2 | 7/2011 | Callister et al. | |
| 8,052,637 B2 | 11/2011 | Von Oepen et al. | |
| 9,498,195 B2 | 11/2016 | Schutt et al. | |
| 2005/0192616 A1 | 9/2005 | Callister et al. | |
| 2006/0206199 A1 | 9/2006 | Churchwell et al. | |
| 2010/0280546 A1 * | 11/2010 | Campbell | A61B 17/0057 606/213 |
| 2017/0127929 A1 | 5/2017 | Schutt et al. | |
| 2018/0289939 A1 | 10/2018 | Mason et al. | |

* cited by examiner

*Primary Examiner* — Emily L Schmidt
*Assistant Examiner* — Samuel J Marrison
(74) *Attorney, Agent, or Firm* — Workman Nydegger

(57) ABSTRACT

An access closure device for closing an opening in tissue is provided. The access closure device may comprise a balloon delivery system and a sealant delivery system. The balloon delivery system may comprise a suture, a delivery shaft, an inflatable balloon, and a balloon segment releasably attached to the delivery shaft. The sealant delivery system may comprise a sealant delivery shaft, an ejection tube, and a snare wire configured to snare a suture of the delivery system.

15 Claims, 16 Drawing Sheets

Conical balloon

Square balloon

Spherical balloon

Conical/square balloon

Conical/square long balloon

Conical/spherical long balloon

Long spherical balloon

Tapered balloon

Dog Bone balloon

Stepped balloon

Offset balloon

Conical/offset long balloon

ACCESS CLOSURE DEVICE

CROSS REFERENCE

This application claims benefit and priority to U.S. Provisional Patent Application No. 63/114,214, filed Nov. 16, 2020, the entire contents of which are incorporated by reference herein.

BACKGROUND

1. The Field of the Invention

The present disclosure relates generally to systems, devices, and methods for blocking an opening in body lumens. More particularly, the present disclosure relates to techniques for percutaneous closure of arterial and venous puncture sites, which are usually accessed through a tissue track.

2. The Relevant Technology

A number of diagnostic and interventional vascular procedures are now performed translumenally. A catheter is introduced to the vascular system at a convenient access location and guided through the vascular system to a target location using established techniques. Such procedures require vascular access, which is usually established using the well-known Seldinger technique and the accelerated variant of the Seldinger technique. For example, angiography, insertion of chest drains and central venous catheters, insertion of PEG tubes, insertion of leads for an artificial pacemaker or implantable cardioverter-defibrillator, insertion of mitral valve clips, and other techniques may be performed using certain principles of the Seldinger technique. Vascular access is generally provided through an introducer sheath, which is positioned to extend from outside the patient body into the vascular lumen. When vascular access is no longer required, the introducer sheath is removed and bleeding or oozing at the puncture site or access track stopped.

One common approach for providing hemostasis (the cessation of bleeding) is to apply external force near and upstream from the puncture site, typically by manual compression. This approach suffers from a number of disadvantages. For example, the manual compression procedure is time consuming, frequently requiring one-half hour or more of compression before hemostasis is achieved. Additionally, such compression techniques rely on clot formation, which can be delayed until anticoagulants used in vascular therapy procedures (such as for heart attacks, stent deployment, and the like) wear off. The anticoagulants may take two to four hours to wear off, thereby increasing the time required before completion of the manual compression procedure.

Further, the manual compression procedure is uncomfortable for the patient and frequently requires analgesics to be tolerable. Moreover, the application of excessive pressure can at times totally occlude the underlying blood vessel, resulting in ischemia and/or thrombosis. Following manual compression, the patient typically remains recumbent from four to as much as twelve hours or more under close observation to assure continued hemostasis. During this time, renewed bleeding may occur, resulting in blood loss through the track, hematoma and/or pseudo-aneurysm formation, as well as arteriovenous fistula formation. These complications may require blood transfusion and/or surgical intervention.

The incidence of complications from the manual compression procedure increases when the size of the introducer sheath grows larger, and/or when the patient is anticoagulated. The compression technique for arterial closure can be risky, is expensive to the hospital and onerous to the patient. Although the risk of complications can be reduced by using highly trained individuals, dedicating such personnel to this task is both expensive and inefficient. Nonetheless, as the number and efficacy of translumenal diagnostic and interventional vascular procedures increase, the number of patients requiring effective hemostasis for a vascular puncture continues to increase.

While certain hemostasis aids have been proposed for use internally in a vessel, there is a problem of internal hemostasis devices being difficult to accurately position proximate a puncture site, difficult to guide into the lumen through a delivery sheath or catheter, and/or potentially hazardous if the hemostasis device breaks loose and travels through the lumen, which can create an embolization risk. There is also a difficulty in forming internal hemostasis aids or devices so as to cooperate effectively with a corresponding sealant device, such as a polymeric sealant or a suture.

There is further a problem of existing access closure devices and methods having rigid or small anchors that risk displacement of arterial plaque. Such anchors may also provide inadequate hemostasis at the intimal puncture.

BRIEF SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Embodiments of the present invention provide systems, methods, and devices for closing an opening in tissue. Embodiments of the invention can be configured to close an opening of a body lumen.

In an embodiment, an access closure device is configured to provide for immediate hemostasis at a vessel puncture site by delivery of a compliant or semi-compliant balloon in a body lumen proximate an access track formed by the insertion of a device, such as a catheterization procedure. The balloon may be molded from one or more biocompatible materials, such as bioabsorbable, biodegradable, or bioresorbable materials, such that the balloon may be left in the body lumen, mitigating the need to withdraw the balloon through the access track. This advantageously accelerates the hemostasis process as the access track may be sealed without deflating and withdrawing a hemostasis device therethrough.

The balloon may cooperate with one or more access track sealants to achieve hemostasis before a procedural sheath is removed. The balloon and/or access track sealants may further cooperate with a suture. The suture may be bioresorbable to maintain position and prevent embolization.

The balloon may have a spherical, cylindrical, or cylindrical tapered shape as suitable, and may have a smooth or textured surface. The surface of the balloon may be configured to effect a desired degree of friction for gripping an inner surface of the lumen wall proximate the access track. For example, the balloon may have a textured surface to help maintain the balloon at the access track even as blood or other fluid flows about the balloon. The balloon may include or cooperate with one-way valves that permit inflation but resist deflation, thereby facilitating the inflation of the balloon from an uninflated configuration during delivery to an inflated configuration when positioned within the body lumen, and ensuring that the balloon remains in the inflated configuration when positioned at the access track.

A delivery system of the access closure device is configured to deliver the balloon within the body lumen. A fluid for inflating the balloon within the lumen may be provided through a lumen of a shaft of the delivery system. The delivery system may include or cooperate with a syringe for delivering the fluid to inflate the balloon when the balloon has been inserted within the body lumen.

The balloon may be deliverable and operable by a balloon segment configured to releasably or frangibly attach to a shaft of the delivery system, such as at a distal end of the shaft of the delivery system. The balloon segment may include a lumen configured to be in fluid communication with the lumen of the delivery system shaft. The balloon segment may further include a plurality of openings in fluid communication with an interior of the balloon and the lumen and a valve selectively sealing the lumen of the balloon segment The delivery system may be configured to releasably support the balloon in an uninflated configuration at a distal end of the delivery system shaft. The delivery system shaft may disengage from the balloon after inflation of the balloon to position the balloon at the access track on the inner surface of the body lumen. The delivery system may include a bypass tube and a handle assembly that can be operated as described herein to inflate and/or detach the balloon.

The access closure device may further include a sealant delivery system. The sealant delivery system may be configured to deliver a sealant within an access track by injecting or positioning a sealant into the access track while the balloon provides occlusion of the access track. The sealant may be delivered through the same lumen as the fluid for inflating the balloon or through a distinct lumen of a distinct shaft.

The delivery system may include one or more weeping ports proximate the balloon. The weeping ports may be connected to a valve such as a check valve configured to, once the inflation pressure of the balloon exceeds a certain threshold, release sealant solution into the access track. The sealant solution may have a gelling or crosslinking component, composition, or mechanism such that the sealant solution has a low viscosity for high injection and a high viscosity for sealing.

The sealant may alternatively be formed as a solid, preformed cylinder or other solid mass that is pushed into place over a tensioning suture. The solid sealant may include one or more of polyethylene glycol (PEG), hyaluronic acid, gelatin, and collagen. As the solid sealant is positioned within the access track, the sealant absorbs fluid and swells, thereby sealing the access track and effecting hemostasis.

A method of using an access closure device according to the disclosed embodiments includes one or more of the following steps: first, a guidewire is removed from a procedural sheath. The delivery system is then advanced into the procedural sheath.

When the delivery system has been advanced to a desired location, the balloon, located at a distal end of the delivery system shaft, is partially inflated. The desired location of the delivery system may be a location where the balloon is located entirely within a body lumen and is not directly adjacent to an inner surface of the body lumen.

The delivery system is then tracked to a second position at which the balloon contacts a tip of the sheath. The delivery system and sheath are tracked together until resistance is encountered at the wall of the lumen.

The sheath is then tracked to a predetermined reference line on an outer surface of the delivery system shaft. The delivery system suture is tensioned while tracking the balloon until resistance is felt. The bypass tube is advanced into the sheath valve to allow a desired degree of blood and fluid flow from the access track for a practitioner to visualize a degree of hemostasis.

The balloon is further inflated until hemostasis is determined to be satisfactory, for example, on the basis of blood flow through the bypass tube. Once hemostasis is satisfactory, the balloon segment is ejected, and the sheath and delivery system are removed from the access track.

The suture is snared, and the sealant is advanced. The suture is cut and sealed either by a mechanical crimp or by heat. In a final step, the suture is taped or otherwise secured to the skin surface, anchoring the balloon in place proximate access track.

In another embodiment of the present disclosure, an access closure device and method provide for extravascular hemostasis at a puncture site with fewer steps than existing modalities. The access closure device may include an implant configured to be positioned by a practitioner at an access track of a puncture site for secure closure of the site.

The implant may include a compliant or semi-compliant implant configured to be anchored in place by a suture, which may also be one or more biocompatible materials, such as bioabsorbable, biodegradable, or bioresorbable materials. The implant may also include at least one sealant material configured to be delivered proximate the implant and/or within the access track for further ensuring hemostasis in cooperation with the implant. The implant additionally may comprise at least one knotted suture or cleat to secure the implant in position.

The implant may include or cooperate with a closure system, including at least an over-the-wire system for security for vascular re-access, and/or a positioning system that provides a blood mark regardless of an access position.

The implant and the suture may be formed by injection molding, compression molding, extrusion, or may be 3D printed, such as by additive manufacturing methods, from one or more biocompatible materials, such as bioabsorbable, biodegradable, and/or bioresorbable polymers. The material from which the implant is formed may be selected on the basis of one or more properties such as strength, stiffness, and rate at which the material compositionally converts into components that are subsequently dispersed within or absorbed by the body after a period of time.

Suitable materials for forming the implant and suture may include one or a combination of a polyglycolic acid (PGA), a poly(L-lactic acid) (PLLA), a polycaprolactone (PCL), a poly(DL-lactic acid) (PDLLA), a poly(trimethylene carbonate) (PTMC), a poly(para-dioxanone) (PPDO), or any other suitable material. It will be understood that in embodiments, the implant and suture may be formed from any suitable material, which may be (i) durable and compatible, or (ii) bioabsorbable, biodegradable, or bioresorbable; such terms describing a material that goes away in the body, while also being biocompatible, or a material that compositionally converts into components that are subsequently dispersed within or absorbed by the body after a period of time.

A method of using an access closure device to deliver an implant according to the disclosed embodiments includes one or more of the following steps: first, the access closure device, comprising a closure system including a sheath through which a guidewire, a suture, and/or a dilator are configured to extend, is positioned within an access track to a body lumen.

The implant is advanced over the guidewire through the sheath until a pulsatile mark is achieved. A dilator may extend through an inner lumen of the sheath and along the guidewire. An exterior surface of the dilator may define through a thickness thereof a marker port through which blood may enter and then flow outwardly through a bleed back lumen. The blood that enters through the marker port may flow to a pulsatile blood mark exterior of the dilator, indicating to the practitioner that the access closure device has successfully entered the body lumen.

After the dilator has been retracted proximally from the sheath and out of the body lumen, the implant may be ejected from the inner lumen of the sheath and into the body lumen by advancing a delivery tube through inner lumen of the sheath. The implant and suture may extend a distance from a distal end of the sheath within the body lumen.

The practitioner may tension the suture, which may extend proximally outward from a proximal end of the sheath, until the implant contacts the distal end of the sheath. With the implant and suture tensioned such that the implant contacts the distal end of the sheath, the sheath may be retracted proximally through the access track. The sheath may be retracted until, for example, the vessel wall is located by contacting the vessel wall with the implant.

When the vessel wall has been located, the sheath may be retracted a further distance. The further distance may be a predetermined distance, which may be provided for ease and precisions of use as one or more indicia on an exterior surface of the sheath. The indicia may be index lines spaced apart by the further distance, such that upon locating the vessel wall, the practitioner may note the current location of the sheath (e.g. by an index line of the sheath corresponding to the surface of the skin) and proceed to retract the sheath to a next index line. This advantageously allows the practitioner to withdraw the implant a desired distance within the access track.

As the sheath is withdrawn by the further distance through the access track, the implant, which may remain positioned at the vessel wall, may again extend by a distance from the sheath. The distance may be a same distance that the implant extended from the sheath within the body lumen, or may be a different distance.

When hemostasis is detected, the guidewire is then retracted through the inner lumen of the sheath. The practitioner may additionally tension the suture until the implant again contacts the sheath tip, the act of tensioning the suture causing the implant to be withdrawn a distance into the access track. In embodiments, the distance may be a predetermined distance, and may be configured to allow the implant to deform and/or extend flush with the vessel wall.

After the implant has been positioned within the access track, the sheath may be retracted, and simultaneously, previously, or subsequently, a sealant material may be delivered along the suture to the access track. After the sealant material has been positioned within the access track as desired, the suture may be trimmed at a desired location, for example at a level of the skin surface. Because of the composition of the implant, sealant, and suture, post-procedure steps and complications, for example, adverse reactions to the plug or steps to remove the suture, are obviated.

By providing an access closure device according to the disclosed embodiments, the problem of existing vessel closure devices and approaches being poorly adapted to providing efficient and effective hemostasis without manual compression is addressed. The access closure device advantageously provides a balloon delivery system for inflating and positioning a balloon at an access track to provide hemostasis and to provide a sealant proximate the balloon in the access track to further effect hemostasis and cooperate with the balloon without having the deflate and remove the balloon through the access track after or while providing the sealant.

The access closure device embodiments also advantageously provide for a vascular closure device that requires fewer and simpler steps for achieving hemostasis without need for manual compression and while minimizing post-procedure steps and complications.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION

Figure 1:
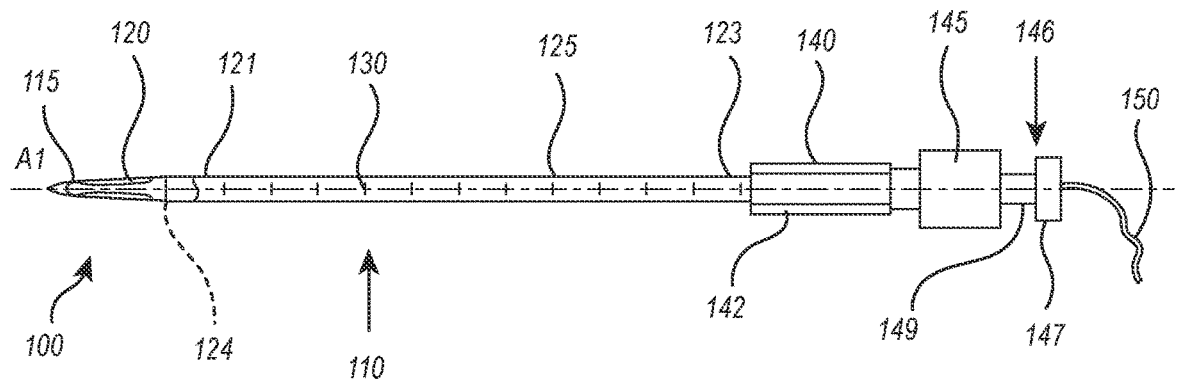
FIG. 1 is a plan view of a balloon delivery system of an access closure device in accordance with one embodiment of the present invention.

One or more specific embodiments of the present disclosure will be described below. In an effort to provide a concise description of these embodiments, some features of an actual embodiment may be described in the specification. It should be appreciated that in the development of any such actual embodiment, as in any engineering or design project, numerous embodiment-specific decisions will be made to achieve the developers' specific goals, such as compliance with system-related and business-related constraints, which may vary from one embodiment to another. It should further be appreciated that such a development effort might be complex and time consuming, but would nevertheless be a routine undertaking of design, fabrication, and manufacture for those of ordinary skill having the benefit of this disclosure.

One or more embodiments of the present disclosure may generally relate to apparatuses, systems, and methods to provide an access closure device configured to close an opening formed in tissue. The apparatuses, systems, and methods can be used to close the opening, with the access closure device remaining within the patient to close the opening and being subsequently absorbed, adsorbed, or resorbed over a period of time.

While the present disclosure will describe a particular implementation of apparatuses and systems, with associated methods, for closing an opening in tissue, it should be understood that any of systems, apparatuses, and methods described herein may be applicable to other uses, including and not limited to closing existing or formed openings in tissue or body lumens in other locations with a patient's anatomy. Additionally, elements described in relation to any embodiment depicted and/or described herein may be combinable with elements described in relation to any other embodiment depicted and/or described herein.

In accordance with the present invention, there is provided an access closure device configured to close an opening formed in tissue, such as a vessel wall of a body lumen, such as an artery. The access closure device may be configured to achieve hemostasis without manual compression or with a reduced duration of manual compression. The access closure device may include an inflatable occlusion balloon configured to be inserted into the body lumen in an uninflated state and inflated in the body lumen. The inflatable occlusion balloon may be positioned proximate an access track (relative to the heart) in the vessel wall formed during a procedure, such as a catheterization or other procedure in which an access track is formed within a wall of a body lumen. In embodiments, the inflatable occlusion balloon may be used in procedures where an access track or orifice already exists. In embodiments, the balloon is configured to be flexible such that the balloon may be inserted into the body lumen and positioned proximate an access track without inflation/deflation operations.

The balloon may be deliverable and operable by a balloon segment configured to releasably or frangibly attach to a shaft of the delivery system, such as at a distal end of the shaft of the delivery system. The balloon segment may include a lumen configured to be in fluid communication with a lumen of the delivery system shaft. The balloon segment may further include a plurality of openings in fluid communication with an interior of the balloon and the lumen and a valve selectively sealing the lumen of the balloon segment. The valve may be a one-way valve to allow for inflation of the balloon and to prevent deflation. The openings may allow for the inflation fluid to inflate the balloon in any desired pattern, shape, or configuration.

The inflatable occlusion balloon may be inflatable using a suitable inflation fluid, which may be saline, a solution of radiopaque contrast agent, sealing solution, or otherwise. In embodiments where a radiopaque contrast agent solution is used to inflate the balloon from the uninflated configuration to the inflated configuration, the contrast solution can be used for visualization by fluoroscopic imaging procedures.

The sealing solution may be configured to seal the access track, as described in greater detail below. The sealing solution may include one or more of polyethylene glycol (PEG), polyethylene oxide (PEO), hyaluronic acid, gelatin, collagen, microfibrillar collagen, microfibrillar collagen with thrombin, gelatin matrix, gelatin matrix with thrombin, oxidized regenerated cellulose, polysaccharide, fibrin sealant, albumin and glutaraldehyde, polyethylene glycol hydrogel, combinations and/or modification thereof. The occlusion balloon may be inflated by use of a syringe operable by a practitioner and/or in fluid communication with the lumen of the delivery shaft and/or the lumen of the balloon segment.

In embodiments, the balloon is formed from a biocompatible material that compositionally converts into components that are subsequently dispersed within or absorbed by the body after a period of time such that the balloon may be safely left within the body lumen and gradually be absorbed, degraded, or resorbed by the patient's body. In embodiments, the balloon is molded from a bioabsorbable, biodegradable, or bioresorbable polymer and the composition of a body of the balloon is chosen to effect a desired strength, stiffness, and/or absorption, degradation, or resorption rate of the balloon. For example, the polymer may be one or a combination of polyglycolic acid (PGA), poly(L-Lactide), polycaprolactone (PCL), copolymers of caprolactone and glycolide, L-Lactide, or D, L-Lactide, poly(D, L-Lactide) (PDLLA), poly(trimethylene carbonate) (PTMC), poly (para-dioxanone) (PPDO), combinations or copolymers thereof, or any other suitable material. In embodiments, the polymer may be selected and configured to be fully resorbed, absorbed, or degraded within a suitable time period, for example, between 1 and 120 days, between 15 and 100 days, between 30 and 90 days, less than 90 days, less than 30 days, or any other suitable time period.

The balloon may be deployable within the body lumen by way of a balloon segment that may be releasably connected to a distal end of a delivery shaft. The release of the balloon segment may be facilitated by a keyed connection, a low force press fit, an adhesive bond that is overcome by a mechanical push tube inserted in an inner diameter of the delivery system shaft, or by any other suitable mechanism. The balloon segment may be formed from a same material as the balloon or may be formed from a different material.

The balloon may be formed by extruding a tube and using a combination of heat and pressure to blow the balloon inside of a balloon mold. The balloon may be formed to have a spherical, cylindrical, cylindrical tapered shape, conical, square shape, combinations and/or modifications thereof, may be symmetric or asymmetric as suitable, and may be coaxially or offset relative to a longitudinal axis, including but not limited to the balloons illustrated in FIGS. 24A-24L. The balloon may further be formed to have any suitable texture on an outer surface, such as a substantially smooth surface, a substantially textured surface, discrete sections having different textures, or any other suitable texture or pattern of textures. The textured surface may comprise a plurality of projections extending outwardly from a surface of the balloon.

The access closure device may further include a sealant delivery system to cooperate with the balloon delivery system. The sealant delivery system may overlap with the balloon delivery system such that a sealant may be delivered to the access track through a same shaft as the balloon; that is, the sealant may be delivered through a lumen of the shaft on the distal end of and by which the balloon and balloon segment are releasably attached and inserted into the body lumen. Particularly in embodiments in which the inflation fluid of the balloon is the sealing fluid or solution, the balloon delivery shaft may include or cooperate with one or more weeping ports positioned proximate the balloon and the balloon segment. The one or more weeping ports may include or cooperate with a check valve configured to release sealant solution into the access track after the balloon inflation pressure exceeds a predetermined threshold.

In embodiments, the sealant delivery system may include a distinct shaft defining an internal lumen through which sealant, such as a sealant solution, may be provided to the access track. The sealing fluid or solution may have a gelling or crosslinking mechanism or component such that the sealing solution may have a low viscosity to facilitate ease of injection and a high viscosity for sealing within the access track. The sealing solution may be or include a two-part system that is pre-mixed prior to administering the sealing solution, in which a first part is a first polymer precursor, and a second part is a second polymer precursor configured to create a desired sealing solution when mixed with the first polymer precursor. One or both of the first and second polymer precursors may be configured or selected to have or be a gelling or crosslinking component.

In embodiments, the sealant delivery system includes a solid and/or preformed structure that can be pushed into place over a tensioning suture within the access track. The structure may have any suitable shape, such as a cylindrical shape, a rectangular shape, a spherical shape, conical shape, combinations and/or modifications thereof, whether or not the shape is coaxially or offset relative to a longitudinal axis or otherwise. The structure may include any suitable sealant material, including one or a combination of a crosslinked PEG, hyaluronic acid, gelatin, and/or collagen, or any other suitable material. The structure may be formed and configured to absorb body fluid, such as blood, and swell, thereby expanding to fill the access track and provide hemostasis. This is particularly effective when provided in combination with the balloon of the disclosed embodiments, as the balloon is configured and positioned to limit or control an amount of fluid that can enter the access track.

In another embodiment of an access closure device and method, extravascular hemostasis is provided at a puncture site with fewer steps than existing access-closure modalities. The access closure device may comprise an implant configured to be positioned by a practitioner at an access track of a puncture site for secure closure of the site without the need for manual compression. The access closure device may further provide a positioning system that provides a blood mark regardless of the access position.

The implant may comprise a compliant or semi-compliant implant configured to be anchored in place by a suture, which may also be bioabsorbable, biodegradable, or bioresorbable. The implant may also include at least one sealant material configured to be delivered proximate the implant and/or within the access track for further ensuring hemostasis in cooperation with the implant. The implant additionally may include at least one knotted suture or cleat to secure the implant in position.

The implant may include or cooperate with a closure system, including at least an over-the-wire system for security for vascular re-access, and/or a positioning system that provides a blood mark regardless of an access position.

The implant and the suture may be bioabsorbable, biodegradable, or bioresorbable and may be formed by injection molding, compression molding, extrusion or may be 3D printed, such as by additive manufacturing methods, from one or more bioabsorbable, biodegradable, or bioresorbable materials, such as bioabsorbable, biodegradable, or bioresorbable polymers. The material from which the implant is formed may be selected on the basis of one or more properties such as strength, stiffness, and absorption, resorption, or degradation rate.

Suitable materials for forming the implant and suture may include one or a combination of a polyglycolic acid (PGA), a poly(L-lactic acid) (PLLA), a polycaprolactone (PCL), a poly(DL-lactic acid) (PDLLA), a poly(trimethylene carbonate) (PTMC), a poly(para-dioxanone) (PPDO), or any other suitable material. It will be understood that in embodiments, the implant and suture may be formed from any suitable material, which may be (i) durable and biocompatible, or (ii) bioabsorbable, biodegradable, or bioresorbable; such terms describing a material that goes away in the body, while also being biocompatible.

A method of using an access closure device to deliver an implant according to the disclosed embodiments includes one or more of the following steps: first, the access closure device, comprising a closure system including a sheath through which a guidewire, a suture, and/or a dilator are configured to extend, is positioned within an access track to a body lumen.

The dilator is advanced over the guidewire through the sheath until a pulsatile mark is achieved. A dilator may extend through an inner lumen of the sheath and along the guidewire. An exterior surface of the dilator may define through a thickness thereof a marker port through which blood may enter and then flow outwardly through a bleed back lumen. The blood that enters through the marker port may flow to an aperture and form a pulsatile blood mark exterior of the dilator, indicating to the practitioner that the access closure device has successfully entered the body lumen.

After the dilator has been retracted proximally from the sheath and out of the body lumen, the implant may be ejected from the inner lumen of the sheath and into the body lumen by advancing a delivery tube through the inner lumen of the sheath. The implant and suture may extend a distance from a distal end of the sheath within the body lumen.

The practitioner may tension the suture, which may extend proximally outward from a proximal end of the sheath, until the implant contacts the distal end of the sheath. With the implant and suture tensioned such that the implant contacts the distal end of the sheath, the sheath may be retracted proximally through the access track. The sheath may be retracted until, for example, the vessel wall is located by contacting the vessel wall with the implant.

When the vessel wall has been located, the sheath may be retracted a further distance. The further distance may be a predetermined distance, which may be provided for ease and precisions of use as one or more indicia on an exterior surface of the sheath. The indicia may be index lines spaced apart by the further distance, such that upon locating the vessel wall, the practitioner may note the current location of the sheath (e.g., by an index line of the sheath corresponding to the surface of the skin) and proceed to retract the sheath to a next index line. This advantageously allows the practitioner to withdraw the implant a desired distance within the access track.

As the sheath is withdrawn by the further distance through the access track, the implant, which may remain positioned at the vessel wall, is configured to extend to an implant configuration. The implanted configuration may be a folded configuration in which a surface of the implant remains at the vessel wall and/or flush therewith, while a remainder of the implant extends within the access track, preventing blood flow from the body lumen into the access track.

If hemostasis is detected, the guidewire is then retracted through the inner lumen of the sheath. The practitioner may additionally tension the suture until the implant again contacts the sheath tip, the act of tensioning the suture causing the implant to be withdrawn a distance into the access track. In embodiments, the distance may be a predetermined distance, and may be configured to allow the implant to deform and/or extend flush with the vessel wall.

After the implant has been positioned within the access track, the sheath may be retracted, and simultaneously, previously, or subsequently, a sealant material may be delivered along the suture to the access track. After the sealant material has been positioned within the access track as desired, the suture may be trimmed at a desired location, for example, at a level of the skin surface. Because of the composition of the implant, sealant, and suture, post-procedure steps and complications, for example, adverse reactions to the implant or steps to remove the suture, are obviated.

FIG. 1 illustrates one example embodiment of an access closure device 100. The access closure device 100 may include a balloon delivery system 110 and a distinct sealant delivery system 160. The balloon delivery system 110 includes a delivery shaft 125 that is generally elongate and extends along an axis A1 from a distal end 121 to a proximal end 123. The delivery shaft 125 may be formed of any suitable material, such as a polymeric material affording the delivery shaft 125 a desired degree of flexibility within a body lumen, such as a femoral artery. The delivery shaft 125 may define an internal lumen through which a suture 150 may extend.

Proximate the distal end 121 of the delivery shaft 125, a balloon segment 120 may be releasably attached to the delivery shaft 125. The balloon segment 120 may include a substantially elongate component extending substantially continuously with and from the delivery shaft 125 when the balloon segment 120 is attached to the delivery shaft 125. The balloon 115 may extend about an exterior surface of the balloon segment 120, for example substantially circumferentially about the balloon segment 120. This may advantageously allow the balloon 115 to expand substantially symmetrically when the balloon 115 has been properly inserted into the body lumen. The balloon 115 may be frangible relative to the balloon segment 120 or may be substantially continuous therewith and configured to not separate therefrom. The balloon segment 120 may connect to a lumen of the delivery shaft 125 which is configured to deliver an inflation fluid from a syringe (not shown) to the balloon segment 120 and the balloon 115. In embodiments, the delivery shaft 125 and the balloon segment 120 are formed continuously with each other as a single component, with a portion defined on the combined delivery shaft/balloon segment at a predetermined location such that upon an actuating motion, such as rotation or pulling by the practitioner, the portion breaks or severs and the balloon segment 120 detaches from the delivery shaft.

The delivery shaft 125 may include one or more indicia 130 on an outer surface thereof. The indicia 130 may serve as reference markers for a practitioner when withdrawing the delivery system 110 from a sheath, as described in greater detail herein. The indicia 130 may be provided in any suitable interval or system. For example, the indicia 130 may be defined at regular spacings, such as centimeters and millimeters. The indicia 130 may alternatively have predefined distances that correspond to a heuristic, such as a generally accepted insertion depth within the body lumen and a generally accepted withdrawal depth when deploying the balloon 115.

Proximate a proximal end 123 of the shaft 125 a bypass tube 140 is attached. The bypass tube 140 may advantageously serve to be advanceable into the lumen of a procedural sheath to visualize hemostasis. The bypass tube 140 may have any suitable configuration, such as a substantially cylindrical configuration that corresponds to an inner diameter of the procedural sheath. The bypass tube 140 may define one or more texture features 142, such as a rib and/or corresponding groove, configured to grip an inner surface of the procedural sheath. In embodiments, bypass tube 140 is configured to allow blood flow between the inner surface of the procedural sheath and the bypass tube 140 or through the bypass tube 140 to indicate whether hemostasis has been achieved. That is, as blood continues to flow, the practitioner continues to position the balloon 115 to achieve a desired degree of hemostasis.

The system 110 may additionally include a hub member 145 and a handle assembly 146. The handle assembly 146 may include a grip portion 147 and an elongate portion 149. The hub member 145 and the handle assembly 146 may be configured to allow a practitioner to manipulate the delivery shaft 125 and to deploy the balloon segment 120. The handle assembly 146, in particular the elongate portion 149, may be operably connected to the hub member 145 by any suitable mechanism, such as a projection between the elongate portion 149 and the hub member 145.

In embodiments, the hub member 145 and/or the handle assembly 146 may actuate an actuator 124 that extends through an inner lumen of the delivery shaft 125 to, for example, release the balloon segment 120 at a desired time. The hub member 145 may actuate and release the balloon segment 120 by, for example, being rotated a predetermined amount by the handle assembly 146. The hub member 145 and/or the handle assembly 146 may define indicia that show a practitioner a predetermined degree of rotation that will effect a release of the balloon segment 120.

A suture 150 may extend through a lumen defined in one or more of the delivery shaft 125, the bypass tube 140, the hub member 145, and the handle assembly 146. The suture 150 may be formed of a bioabsorbable, biodegradable, or bioresorbable material such as described above and may be configured to be fully absorbed, resorbed, or degraded within a predetermined time period, which may correspond to the time period determined for absorption of the balloon 115 and the balloon segment 120.

Figure 2:
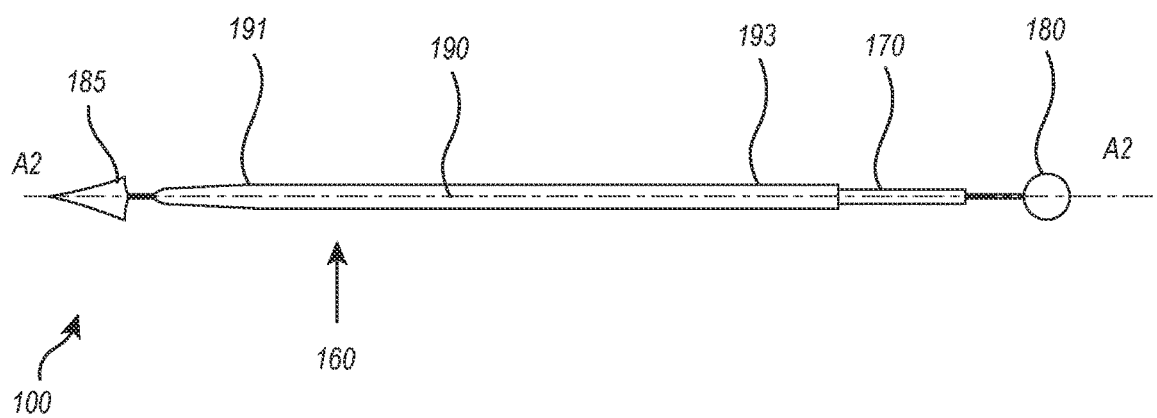
FIG. 2 is a plan view of a sealant delivery system of the access closure device according to the embodiment of FIG. 1.

As seen in FIG. 2, a sealant delivery system 160 may include a distinct sealant delivery shaft 190 extending generally longitudinally from a distal end 191 to a proximal end 193 about an axis A2. The sealant delivery shaft 190 may define an inner lumen within which an ejection tube 170 may be configured to extend and longitudinally translate relative to the sealant delivery shaft 190. The ejection tube 170, likewise, may define an inner lumen through which a snare wire 180 may be configured to extend. The snare wire 180 may terminate proximate the distal end 191 with a snare component 185, which may be shaped in a triangular, diamond, or other suitable shapes for grasping the suture 150 within the body lumen or the access track.

The inner lumen of the sealant delivery shaft 190 may be configured to receive and hold a sealing solution, such as a fluid or solution may have a gelling or crosslinking mechanism or component such that the sealing solution may have a low viscosity to facilitate ease of injection and a high viscosity for sealing within the access track. In embodiments in which the sealing fluid is a two-part mixture, corresponding syringes or delivery devices for each part of the two-part mixture may be provided in fluid communication with the sealant delivery shaft 190 or separately therefrom. The sealing fluid may include as many or as few components and corresponding mechanisms as suitable.

The snare wire 180 may be formed of any suitable material, such as metal, plastic, combinations thereof, or otherwise. For example, the snare wire 180 may be formed from one or more of corrosion resistant materials, stainless steel, such as 300 series stainless steel, steel, cobalt chromium, titanium, platinum, alloys, such as nickel-titanium, a coated material, with suitable coatings including gold or silver, or combinations and/or modifications thereof. Suitable plastics may include polyvinyl chloride, polyurethane, polypropylene, polyethylene terephthalate (PET), poly(tetrafluoroethylene), nylon, and others. In embodiments, the snare wire is formed of bioabsorbable, biodegradable, or bioresorbable materials. The snare wire 180 may be configured to cooperate with the suture 150, as will be described herein.

Figure 3:
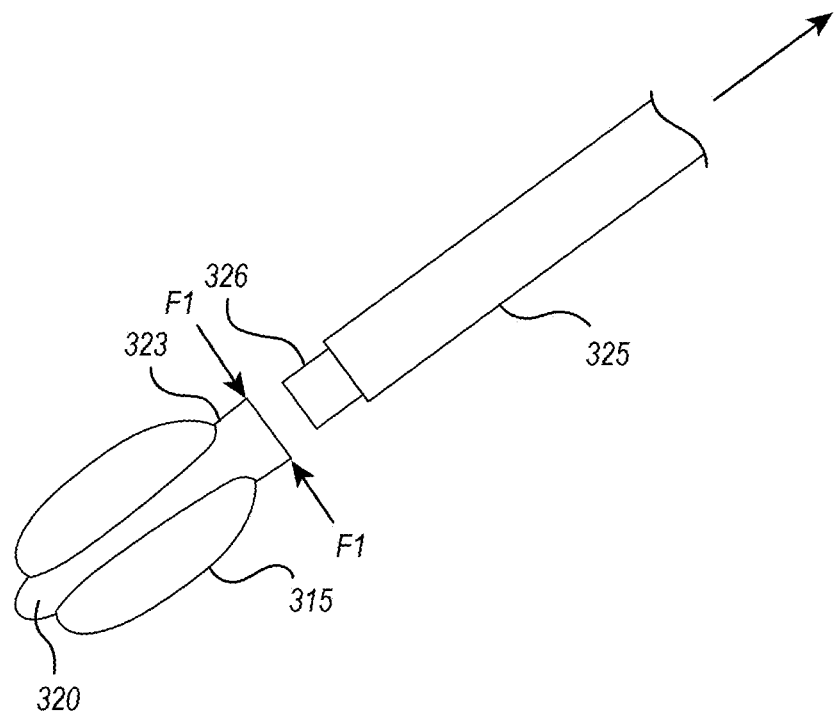
FIG. 3 is a perspective view of a balloon delivery system of an access closure in accordance with an embodiment of the present invention.

FIGS. 3,-4 and 5A-5C illustrate embodiments of an attachment between a balloon segment and a delivery shaft as described above. In FIG. 3, a balloon segment shaft 323 is configured to press-fit with a delivery shaft 325 of a delivery system as described herein. An extension portion 326 of the delivery shaft 325 may have a reduced diameter compared to a length of the delivery shaft 325 and may be configured to mate and engage with a recess defined in at least a portion of a thickness of the balloon segment shaft 323.

The balloon segment shaft 323 and the delivery shaft 325 may be formed from materials with a predetermined friction coefficient that provides for a reliable attachment of the balloon segment 320 to the delivery shaft 325 while also facilitating a desired detachment by any suitable mechanism when the delivery system is to be withdrawn from the access track. In particular, a first force F1 exerted by the walls of the access track against the extension portion 326 may retain the delivery shaft 325 and the balloon segment 320 in an engaged configuration, whereas if a second force F2 transverse to the first force F1 and in a longitudinal direction of the delivery shaft 325 exceeds the first force F1, the delivery shaft 325 may disengage from the balloon segment 320 and leave the balloon segment 320 and the balloon 315 in situ. Alternatively, the extension portion 326 may retain the delivery shaft 325 by an adhesive bond, complementary surface finishes, detents, keyways, other interference fit structures, combinations and/or modifications thereof.

Figure 4:
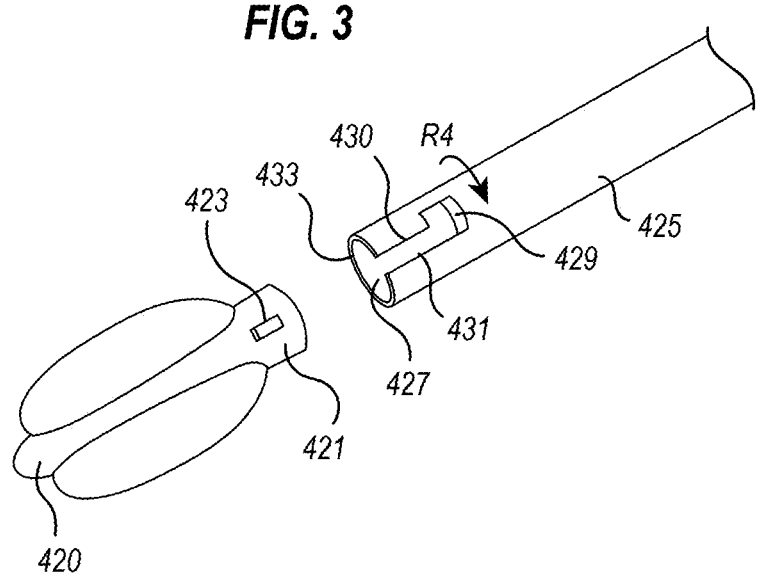
FIG. 4 is a perspective view of a balloon delivery system according to another embodiment of the present invention

In an alternative embodiment shown in FIG. 4, the balloon element 420 may be provided with an extension portion 421 configured to fit within a lumen 427 defined by a delivery shaft 425. The delivery shaft 425 may define a keyway or channel 431 configured to cooperate with a key element 423 defined on the extension portion 421. The key element 423 may be a protrusion extending outwardly from the surface of the extension portion 421.

The keyway 431 includes a channel 430 that extends substantially longitudinally and extends to a distal edge 433 of the delivery shaft 425. The keyway 431 further includes a channel 429 connected to the channel 430 and extending substantially circumferentially. In operation, the balloon element 420 attaches to the delivery shaft 425 by the extension portion 421 extending within the lumen 427 of the delivery shaft 425. The extension portion 421 is held in place relative to the delivery shaft 425 as the key element 423 prevents longitudinal movement of the extension portion 421 out of the lumen 427 when the key element 423 is in the channel 429. When it is desired to detach the balloon element 420, the practitioner may rotate the delivery shaft 425 to achieve relative movement between the delivery shaft 425 and the balloon element 420. For instance, the practitioner may rotate the delivery shaft 425 such that the delivery shaft 425 rotates relative or in relation to the balloon element 420 in a direction R4. The delivery shaft 425 may then be translated in a longitudinal direction such that the balloon element 420 translates relative to the delivery shaft 425 longitudinally through the channel 430 toward the distal edge 433 until the balloon element 420 detaches from the delivery shaft 425 by exiting completely the lumen 427. The disclosed arrangement of the keyway 431 and the key element 423 is merely exemplary, and the configuration may vary in any suitable manner.

Figure 5A:
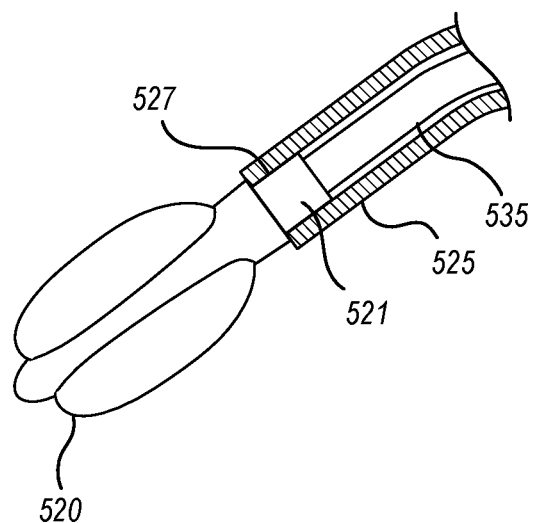
FIGS. 5A-5C are a perspective view of a balloon delivery system according to another embodiment of the present invention.
Figure 5B:
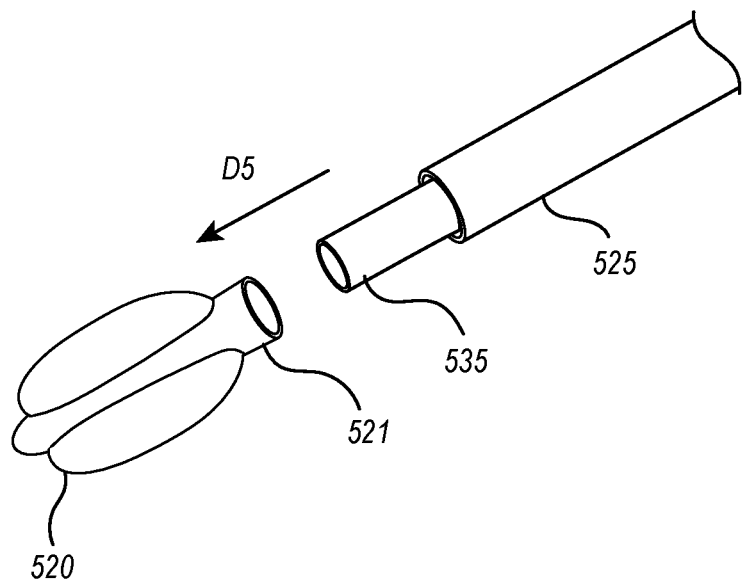
Figure 5C:
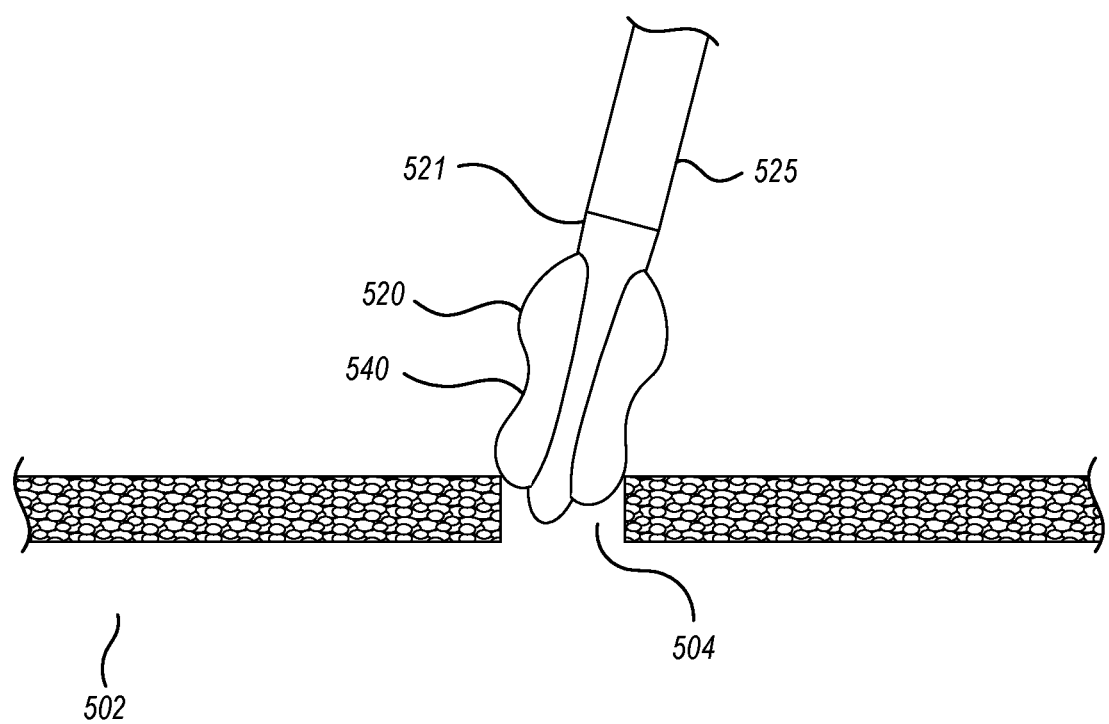

FIGS. 5A-5C illustrate an embodiment of a balloon segment 520 that is actuated by an ejection element or shaft 535 contained in or cooperating with the delivery shaft 525. In the embodiment shown in FIGS. 5A-5C, the delivery shaft 525 defines an inner lumen 527 within which, at a distal end of the delivery shaft 525, an extension portion 521 of the balloon segment 520 is configured to slidingly fit and to remain by a low-force press fit, complementary surface finishes, detents, keyways, other interference fit strategies or structures, faying surfaces having a rough surface finish creating resistance to separation, an adhesive bond against the inner diameter of the inner lumen 527 as shown in FIG. 5A, or combinations and/or modifications thereof.

The ejection shaft 535 may be configured to slide through the inner lumen 527 from a proximal end of the delivery shaft 525. When the practitioner wishes to disengage the balloon segment 520, the practitioner may advance the ejection shaft 535 distally in a direction D5 to push the balloon segment 520 distally out of the lumen 527, as seen in FIG. 5B. It will be appreciated that the disclosed arrangement of the delivery shaft, ejection shaft, and balloon element in the embodiment of FIGS. 5A and 5B is merely exemplary, and the balloon element may be releasably attached to the delivery shaft in any suitable manner.

Turning to FIG. 5C, the balloon segment 520 may be inserted into an access track 504 defined through a thickness of a body lumen 502. The balloon segment 520 may be in a first, uninflated configuration and arranged releasably at a distal end of a delivery shaft 525, as described in reference to one or more of the embodiments of FIGS. 3-4 and 5A-5B. The balloon segment 520 may be formed of any suitable material, including polymeric or elastomeric materials, and may be sufficiently flexible to deform. For example, the balloon segment 520 may deform to an insertion configuration defining a detent or compression region 540 upon the balloon segment 520 being pressed into an access track 504.

The previous figures and the corresponding text provide a number of different components and systems that may be used to close an opening in a body lumen. In addition to the foregoing, other example embodiments may also be described in terms of flowcharts comprising one or more acts in a method for accomplishing a particular result. For example, FIG. 15 illustrates a method 1500 of closing an opening in tissue. The acts of method 1500 are discussed more fully below with respect to the disclosures of FIGS. 6 through 14.

Figure 6:
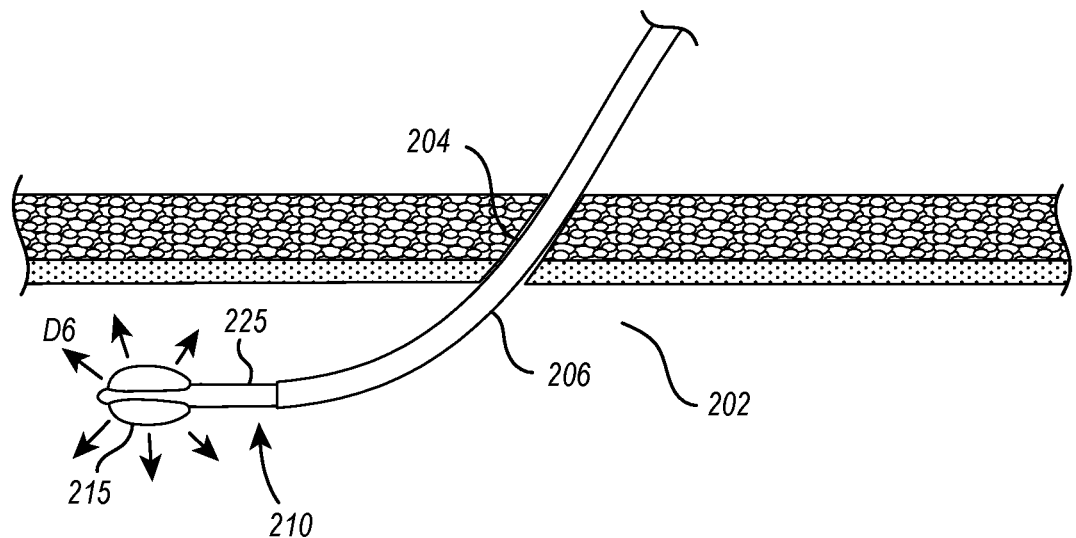
FIGS. 6-14 illustrate the use of an exemplary access closure device according to an embodiment of the present invention.

A method of using an access closure device according to embodiments of the present disclosure is shown in FIGS. 6-14. In FIG. 6, a procedural sheath 206 is advanced into a body lumen 202 through an access track 204, and a guidewire is removed therefrom. The access track 204 may be formed during a procedure such as a catheterization or may be an existing opening. The procedural sheath 206 may be configured in size and properties to fit within the particular body lumen 202, such as a femoral artery, for which the procedural sheath 206 is intended for use. As seen, the procedural sheath 206 may be sufficiently flexible to bend within the body lumen 202 for delivery of a balloon or other occlusion device. As seen, the procedural sheath 206 may fit flush within the access track 204 such that leakage of body fluid, such as blood, does not occur substantially during the described procedure.

A delivery system 210, including a delivery shaft 225, a balloon segment 220 with a valve 222, and a balloon 215, may be provided and may be configured to extend through an internal lumen of the procedural sheath 206. The delivery system 210 may be advanced into the procedural sheath 206 after the aforementioned guidewire is removed from the procedural sheath 206. As the delivery system 210 extends through the procedural sheath into the body lumen 202, the balloon 215 may be partially inflated in outward directions D6 from an original uninflated configuration using any suitable inflation fluid, such as sealing fluid, saline, a solution of radiopaque contrast agent, combinations thereof, or any other suitable inflation fluid. The inflation fluid may be provided under a back pressure from a syringe (not shown) operated by the practitioner.

The partial inflation of the balloon 215 may be assessed as any suitable metric. In embodiments, the balloon 215 is deemed to be partially inflated for the purposes of a first step of the method described herein when a predetermined volume of inflation fluid has been delivered to the balloon 215. Partially inflated may alternatively be determined as a percentage of a total possible volume of the balloon 215, such as 50%. The predetermined partial inflation may be determined as a volume that will prevent the balloon 215 from being withdrawn through the inner lumen of the procedural sheath.

Figure 7:
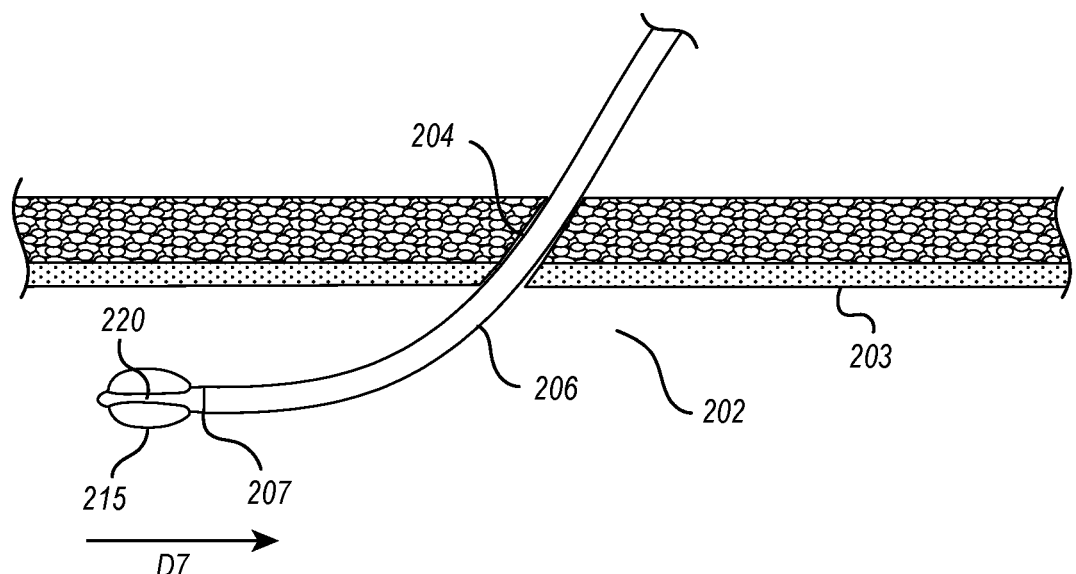

After the balloon 215 has been partially inflated, the delivery system 210 may be retracted proximally in a direction D7 through the inner lumen of the procedural sheath 206 until the balloon 215 contacts a distal tip 207 of the procedural sheath 206, as shown in FIG. 7. The distal tip 207 may be formed as a substantially flat lip of the procedural sheath 206, or the distal tip 207 may be sized and configured to be complementary to a shape of the balloon 215. The partial inflation of the balloon 215 from the uninflated configuration of the balloon 215 prevents the balloon 215, the balloon segment 220, and the delivery system 210, to which the balloon 215 and the balloon segment 220 are still releasably attached, from retracting farther than a contact configuration of the balloon 215 with the distal tip 207 as shown in FIG. 7. As seen, this step of the method may occur while the procedural sheath 206 and the delivery system 210 are within the body lumen 202 and not proximate the access track 204.

Figure 8:
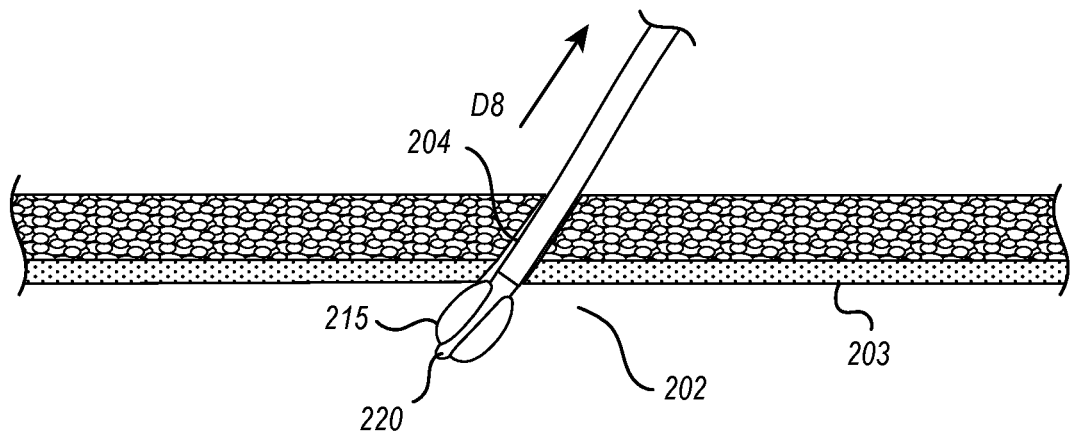

Turning to FIG. 8, after the delivery system 210 has been withdrawn through the inner lumen of the procedural sheath 206 until the partially inflated balloon 215 contacts the distal tip 207 of the procedural sheath 206, such that further withdrawal of the delivery system 210 through the procedural sheath 206 is prevented, the delivery system 210 and procedural sheath 206 are both simultaneously withdrawn in a direction D8 through the access track until resistance is encountered at the vessel wall 203. As seen in FIG. 8, the delivery system 210 and procedural sheath 206 can be withdrawn until the partially inflated balloon 215 contacts the vessel wall 203. The balloon may be partially inflated to a degree that passage of the balloon 215 through the access track 204 is prevented, which may be predetermined on the basis of a volume and size of the balloon 215 and/or a pressure inside of the balloon 215 so as to prevent deformation and unintended deflation of the balloon 215 upon contact with the vessel wall 203 such that inadvertent passage of the procedural sheath 206 and the delivery system 210 through or an undesired degree into the access track 204 is prevented.

Figure 9:
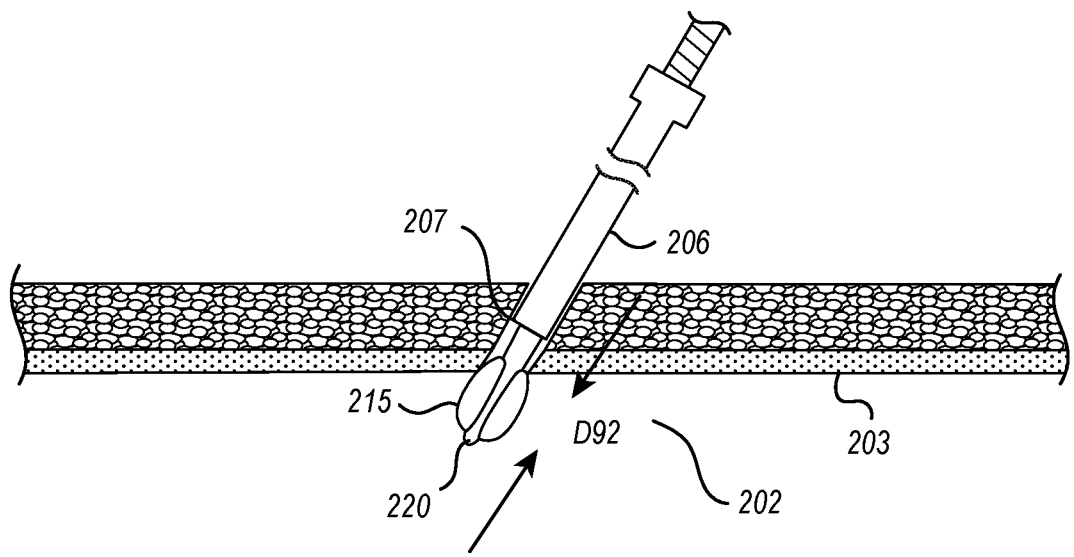

Turning to FIG. 9, after the delivery system 210 and procedural sheath 206 have been withdrawn in a direction D91 until the partially inflated balloon 215 contacts the vessel wall 203, the procedural sheath 206 is withdrawn to a predetermined indicia or reference marker 230 defined on an outer surface of the delivery shaft 225. The predetermined indicia 230 may be any suitable indicia, including a regular measurement interval, such as centimeters and millimeters, or the indicia 230 may be a predetermined suitable distance corresponding to a distance by which the procedural sheath 206 should be withdrawn. As the procedural sheath 206 is withdrawn at the predetermined distance, the delivery shaft 225 remains anchored in place by the placement of the balloon 215. A distance D92 between the balloon 215 and the distal tip 207 of the procedural sheath 206 is created as the procedural sheath 206 is withdrawn.

Figure 10:
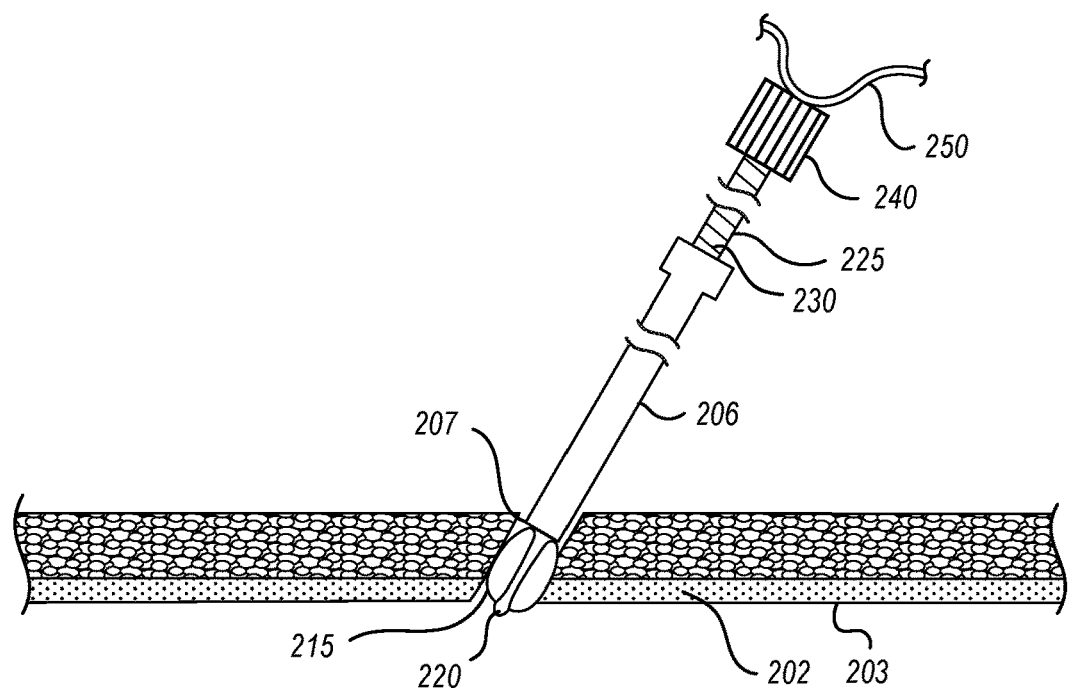

Turning to FIG. 10, a suture 250 of the delivery system 210 is tensioned while retracting the balloon 215 into the access track 204, such that the distance D92 between the balloon 215 and the distal tip 207 is closed, and the balloon 215 again contacts the distal tip 207. As the resistance from the contact between the balloon 215 and the distal tip 207 is felt or generated, the tensioning operation is completed. The balloon 215 may be fully or substantially fully positioned within the access track 204 and removed from the body lumen 202.

Figure 11:
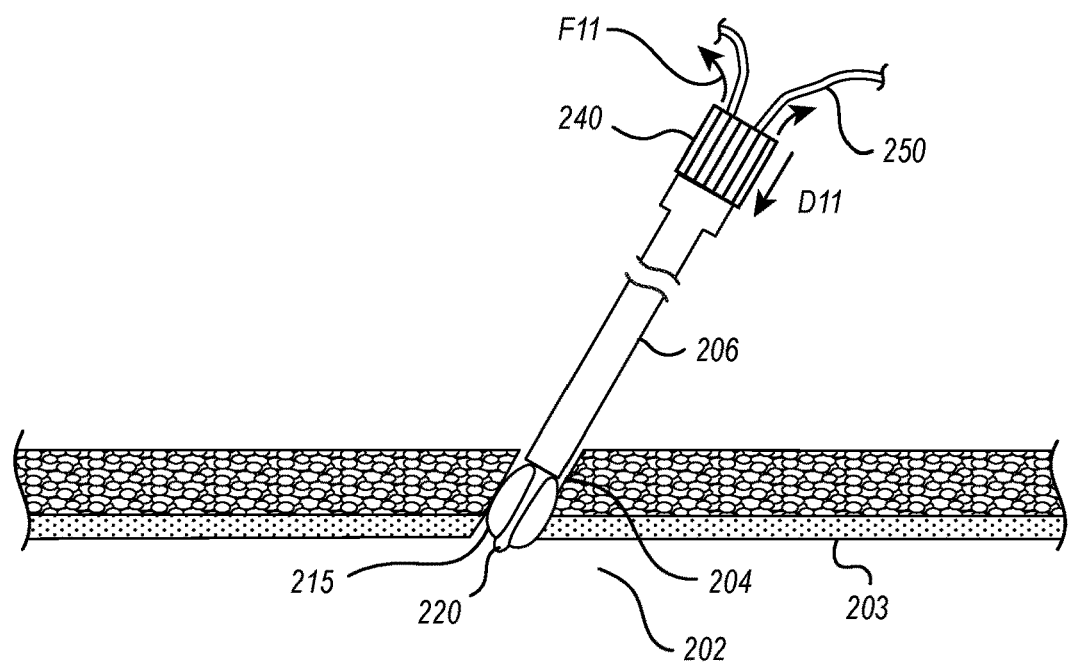

Turning now to FIG. 11, after the balloon 215 again contacts the distal tip 207 and resistance is detected, a bypass tube 240 of the delivery system 210 may be advanced in a direction D11 into contact with the procedural sheath 206. The cooperation of the bypass tube 240 and the procedural sheath 206 is configured to allow blood and fluid flow F11 from the access track 204 and around or through the bypass tube 240, thereby indicating a degree of hemostasis to the practitioner. A continued degree of blood flow F11 through the bypass tube 240 may indicate that hemostasis has not been adequately achieved and indicate to the practitioner to continue positioning the balloon 215 proximate or within the access track 204 to provide improved hemostasis, for example. As will be described in greater detail below regarding FIG. 12, the degree of hemostasis ascertained by the steps performed in FIG. 11 can indicate that additional inflation of the balloon 215 may be required.

Figure 12:
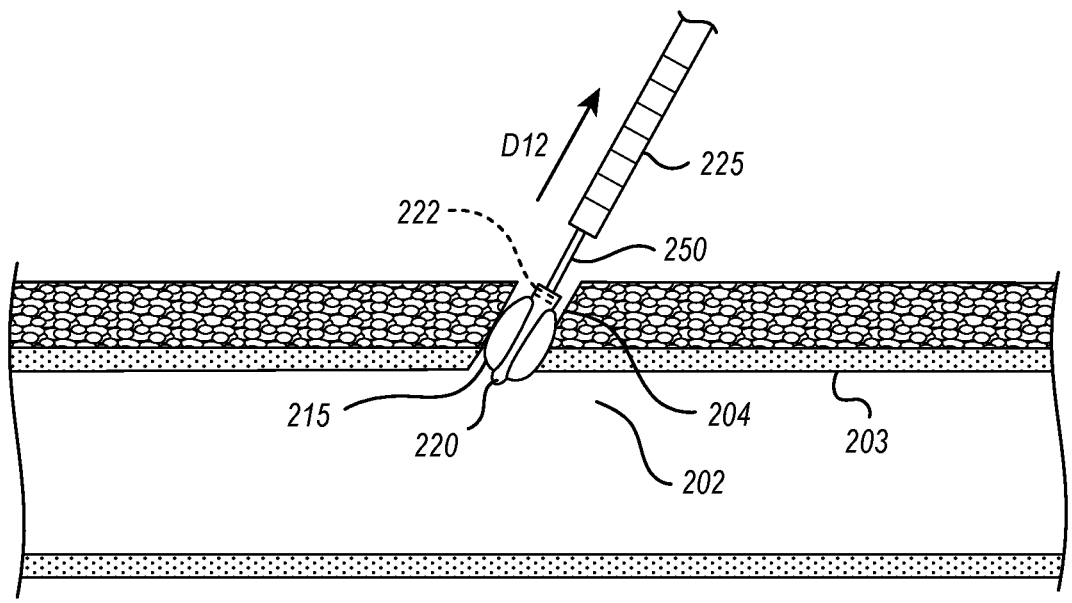

Turning to FIG. 12, the balloon 215 may be further inflated to provide satisfactory hemostasis. The balloon 215 may be inflated by the provision of additional inflation fluid, such as saline, radiopaque contrast agent solution, or sealing solution, and may be administered by back pressure provided by the practitioner through a syringe, which is not shown. The balloon 215 may be configured to be inflated up to a predetermined maximum threshold of volume and/or pressure. The delivery system 210 may be configured to provide an indication to the practitioner that the maximum volume/pressure has been reached. For example, the delivery shaft 225 may be provided with one or more weeping ports (not shown) provided proximate the balloon segment 220, the weeping ports comprising or configured to cooperate with one or more check valves such that upon reaching a predetermined maximum threshold of volume or pressure, the inflation fluid is released into the body lumen 202.

Upon determining that the balloon 215 has been inflated to a desired volume and/or pressure and/or upon determining that a satisfactory hemostasis has been attained, the procedural sheath 206 and then the delivery shaft 225 may be detached and withdrawn from the balloon segment 220. The procedural sheath 206, not being attached to the balloon segment 220, may be first withdrawn in an outward direction D12 from the access track 204. After the removal of the procedural sheath 206, the connection between the delivery shaft 225 and the balloon segment 220 may be severed by any suitable mechanism or procedure to allow the balloon segment 220 and the balloon 215 to remain in the access track 204 and provide hemostasis while the delivery system 210 is released and retracted. For example, a handle assembly 146 and hub member 145, as shown in FIG. 1 may be actuated to release a connection between the balloon segment 220 and the delivery shaft 225, such that only the suture 250 continues to extend between the delivery system 210 and the balloon segment 220. Due to the properties of the fully inflated balloon 215, the access track 204 may remain in an open configuration while maintaining hemostasis, even as blood flows F12 through the body lumen 202.

Figure 13:
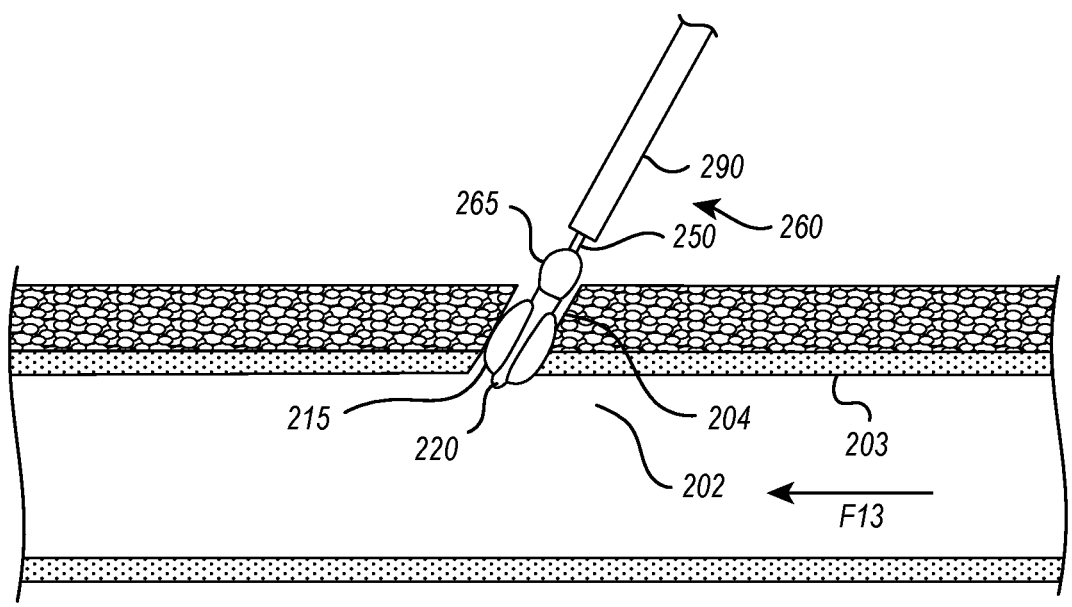

Turning now to FIG. 13, a sealant delivery system 260 comprising a sealant delivery shaft 290 may be advanced along the suture 250 so as to provide a sealant within the access track 204. A sealant plug 265 may be formed within the access track 204 by any suitable mechanism described herein. For example, the sealant plug 265 may be formed by delivering a sealing fluid through an inner lumen of the sealant delivery shaft 290, the sealing fluid comprising one or more polymeric compounds configured to provide hemostasis within the access track 204 being ejected by an ejection tube as shown in FIG. 2. The sealant plug 265 may be a solid structure advanced along the suture 250 after the suture 250 has been snared, and the solid sealant structure may be configured to absorb fluid within the access track 204 so as to expand to fill the space defined by the access track 204.

The sealant delivery system 260 may snare the suture 250 using a snare wire as shown in FIG. 2, where the snare wire 180 includes a snare component 185 having a suitable shape, such as a triangular, diamond, or other shape that allows the snare wire 180 to grasp or otherwise manipulate the suture 250 and to draw the suture 250 outwardly from the access track 204 as the sealant delivery system 260 and the associated snare wire are drawn or tensioned outwardly. The suture 250 may be cut and sealed either by mechanical crimp or by heat after being cut. As described above, the suture 250 may be formed of a bioabsorbable, biodegradable, or bioresorbable material so as to be absorbed, degraded, or resorbed within a desired and suitable time period.

Advantageously, the sealant plug 265 may be formed and established within the access track 204 as the balloon 215 remains in place at the access track 204, providing hemostasis. This allows for the synergistic benefits of providing both an inflatable and bioabsorbable, biodegradable, or bioresorbable balloon at the access track 204 to block flow of fluid into the access track 204 while the sealant plug 265 is established and solidified to further block oozing at the access track 204.

Even further, the balloon 215 need not be deflated back to an uninflated configuration and then withdrawn back through the access track 204, disrupting the solidification of the sealant plug. Blood can flow F13 with minimized risk of thrombus or embolus as the balloon 215 may be arranged to be substantially flush or aligned with the vessel wall 203. While the balloon 215 and the balloon segment 220 are shown extending through a thickness of the vessel wall 203, it will be appreciated that the balloon 215, the sealant plug 265, and other components may extend in any suitable configuration.

Figure 14:
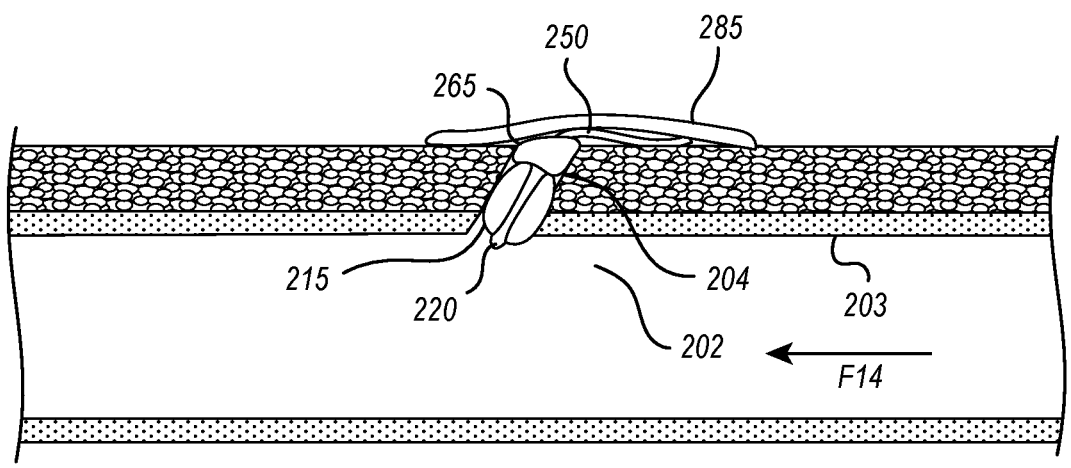
Figure 15:
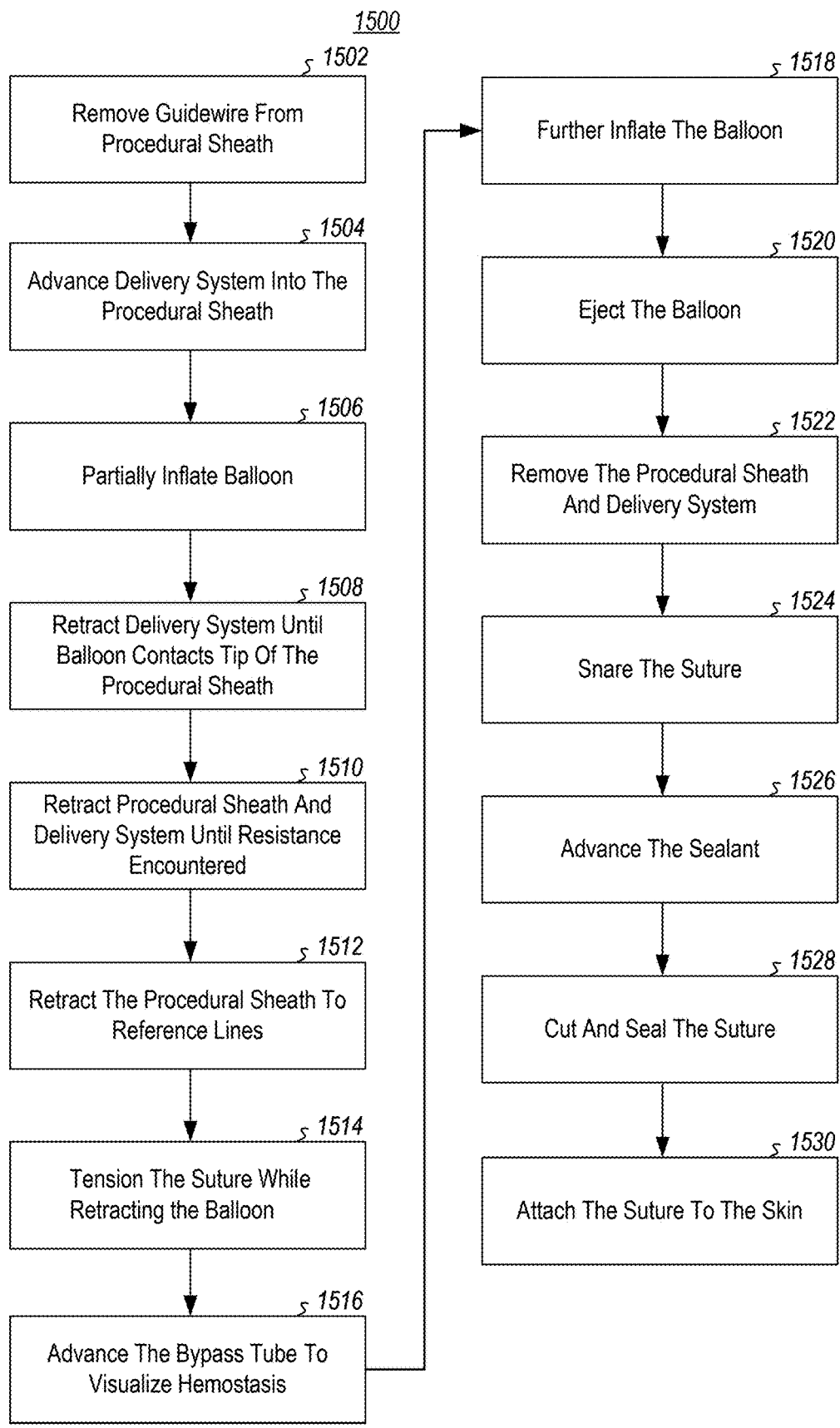
FIG. 15 illustrates a method of using an access closure device according to the embodiment of FIGS. 6-14.

In a final step, FIG. 14 shows a cover 285 that is placed over the now-closed access track 204 to secure the suture 250 to a surface of the patient's skin after the sealant delivery system 260 has been withdrawn from the access track 204 after snaring the suture 250. The cover 285 may be medical tape, a patch, a bandage, or any other suitable cover. The combination of the balloon 215, the balloon segment 220, and the sealant plug 265 advantageously provides hemostasis with minimized or entirely without manual compression, improving patient comfort and outcomes. Blood can flow in the direction of arrow F14 unimpeded and with minimized risk of thrombus or embolus while hemostasis prevents flow of the blood into the access track 204, minimizing a degree of manual compression necessary.

FIG. 15 shows an exemplary method for closing an access track or orifice. The exemplary method 1500 includes one or more of the following steps, not necessarily in the following order. The method 1500 includes a first step 1502 of removing a guidewire from a procedural sheath. As shown regarding the embodiment of FIG. 3, a delivery system comprising a delivery shaft and a balloon element releasably connected to the delivery shaft may be advanced into a lumen of the procedural sheath in a step 1504. The delivery system and the procedural sheath may extend into a body lumen. The delivery system may be advanced a distance such that the balloon element extends past a distal end of the procedural sheath.

At a step 1506 a balloon connected to the balloon element is partially inflated within the body lumen. The balloon is inflated with an inflation fluid which may be one or more of a saline solution, a radiopaque marker solution, a sealing solution, or any other suitable solution. A predetermined volume and/or pressure may be applied to the balloon. The balloon and the balloon element are advantageously formed from bioabsorbable, biodegradable, or bioresorbable materials such that the balloon and balloon element do not need to be removed from the body lumen after closure of the access track.

In a step 1508 the delivery system is retracked outwardly until the distance between the balloon and the distal end of the procedural sheath is narrowed or eliminated. The delivery system may be withdrawn until the balloon contacts the distal edge of the procedural sheath. The delivery system does not translate past this point owing to the size, shape, and/or pressure of the balloon which occludes the lumen of the procedural sheath.

A step 1510 includes retracting the procedural sheath and the delivery system simultaneously until resistance is encountered. The procedural sheath and the delivery system may be retracked outwardly through the access track until the partially inflated balloon occludes the access track at the body lumen inner wall, such that further translation of the procedural sheath and the delivery system is precluded and providing resistance that signals to a practitioner that further translation is not necessary.

A step 1512 includes retracting the procedural sheath a predetermined distance, such as to a predetermined indicium defined or demarcated on an outer surface of the delivery shaft. The procedural shaft is advantageously retracked to provide a distance between the balloon element, which is retained in place at the access track proximate the vessel wall, and a distal tip of the procedural shaft.

A step 1514 of the method 1500 includes tensioning a suture provided in cooperate with the delivery system. The suture may likewise be formed of a bioabsorbable, biodegradable, or bioresorbable material. As the suture is tensioned, the balloon and the balloon element may be withdrawn into the access track such that the balloon extends substantially only within the access track, leaving the body lumen free of obstructions and/or extending flush with a surface of the body lumen.

In a step 1516 of the method 1500, a bypass tube of the delivery shaft is advanced distally toward the access track such that the bypass tube may engage a portion of the procedural sheath and permit a flow of fluid from the access track outwardly. This enables the practitioner to visually ascertain whether hemostasis has occurred. Depending on a flow of blood facilitated by the bypass tube, the practitioner may adjust an inflation of the balloon and/or adjust a position of the balloon.

The method 1500 may also include a step 1518 of further inflating the balloon, for example in response to a determination based on a degree of fluid flow through or around the bypass tube that hemostasis is not yet sufficiently established by the balloon. The balloon may be inflated up to a predetermined threshold volume and/or pressure, which may be determined based on the desired size and properties of the balloon and/or in view of procedural requirements, such as the size of the access track. Additionally, fully inflating the balloon up to the threshold volume and/or pressure advantageously secures the balloon in a desired location of the access track proximate the inner wall of the body lumen, such that the balloon resists displacement from its location owing to the increased friction between the surface of the balloon and the walls of the access track.

A step 1520 may include ejecting the balloon and the balloon segment from the delivery system. The delivery system may eject the balloon and the balloon segment by any suitable mechanism and/or upon an actuation by a practitioner. For example, the practitioner may actuate a hub member and/or a handle assembly as described regarding the embodiment of FIG. 1 to detach the balloon segment from a distal end of the delivery shaft. After ejection of the balloon and the balloon segment, the balloon may remain connected or close only to the suture.

A step 1522 may include removing the procedural sheath and the delivery system after the balloon and the balloon segment have been ejected, with the balloon securing the access track such that hemostasis is maintained upon removal of the procedural sheath and the delivery shaft. The removal of the procedural sheath and the delivery shaft advantageously leaves a majority of the volume of the access track accessible by a practitioner to navigate a sealant delivery system into the access track. In embodiments where the sealant delivery system is integral with the balloon delivery system, the sealant may be delivered or injected into the access track prior to the delivery system being withdrawn at the step 1522.

A step 1524 may include, upon navigating the sealant delivery system into or proximate the access track, snaring the suture. The sealant delivery system, such as a sealant delivery system shown in FIG. 2, may include a snare wire configured to grasp, snare, or otherwise manipulate the suture remaining in the access track and may be operable by an attachment at a distal end of the sealant delivery shaft. The step 1526 of advancing a sealant may be subsequent to, prior to, or simultaneous with the step 1524, and may include advancing a liquid sealing solution, a solid sealant structure, a combination thereof, or any other suitable sealant. The sealant may be a polyethylene glycol (PEG), polyethylene oxide (PEO), hyaluronic acid, and/or gelatin sealant, in embodiments. The sealant advantageously cooperates with the balloon to provide additional hemostasis at the access track to mitigate the need for manual compression.

After the step 1524 of snaring the suture, a step 1528 of cutting and sealing the suture is performed. The suture may be cut and sealed in any suitable manner, such as by a mechanical crimp or by heat. The suture advantageously cooperates with the balloon and the sealant to provide adequate or complete hemostasis without manual compression and without subsequent removal of the balloon. At a final step 1530, the suture, after being cut and sealed, is attached to the skin by a patch or cover. The patch or cover may be a bandage, tape, or other cover that advantageously adheres the suture to a patient's skin. The suture may advantageously maintain a position of the balloon and/or the sealant, and may prevent embolization.

Turning to FIGS. 16-22, another embodiment of an access closure device 600 and a method of using the same is shown. The access closure device 600 may comprise a sheath 605 configured to extend into a body lumen 602 through an access track 604. A flow of blood F16 may flow through the body lumen 602. The sheath 605 may be configured to be advanced through the access track 604 over a guidewire 601. The sheath 605 may additionally cooperate with a suture 608 extending through the inner lumen and connected as discussed in greater detail hereafter to an implant.

The sheath 605 may be substantially elongate and/or formed of any suitable material, such as polymeric and/or elastomeric materials. The sheath 605 may define an enlarged handle portion 606 at a proximal end and terminate at a distal end 607. The sheath 605 may define an inner lumen through which at least a guidewire 601 may extend into the body lumen 602.

The device 600 may be configured with or may cooperate with at least one implant for providing hemostasis. In embodiments, the device 600 may comprise or cooperate with a dilator 610 configured to extend through the inner lumen of the sheath 605. The dilator 610 may likewise be substantially elongate and extend from a handle portion 615 and terminate at a distal end 611. The dilator 610 may be formed of any suitable material, such as polymeric and/or elastomeric materials.

The dilator 610 may have dimensions that allow a practitioner to insert the dilator 610 through the inner lumen of the sheath 605 and into the body lumen 602, with the distal end 611 of the dilator 610 extending distally past the distal end 607 of the sheath 605, and/or with the handle portion 615 of the dilator 610 remaining proximally past and accessible proximally of the handle portion 606 of the sheath 605. In embodiments, the handle portion 615 of the dilator 610 may have a greater diameter than a diameter of the inner lumen of the sheath 605, preventing the handle portion 615 of the dilator 610 from entering the inner lumen of the sheath 605.

In embodiments, the dilator 610 may comprise an inner lumen configured to receive and/or cooperate with a guidewire 601. The guidewire 601 may have sufficient flexibility to be inserted into and navigated through the body lumen 602 and sufficient strength to facilitate the insertion of the sheath 605 and/or the dilator 610. The guidewire 601 may extend through the inner lumen of both the sheath 605 and the dilator 610.

The dilator 610 may further comprise one or more features, including a marker port 612 proximate the distal end 611 of the dilator 610. The marker port 612 may be configured and located such that when the dilator 610 is inserted into the inner lumen of the sheath 605 with the distal end 611 of the dilator 610 extending distally past the distal end 607 of the sheath 605, and/or the handle portion 615 of the dilator 610 contacts the handle portion 606 of the sheath 605, the marker port 612 also extends past the distal end 607 of the sheath 605 and into the body lumen 602.

The marker port 612 may comprise an aperture defined through at least a portion of a thickness of the dilator 610 and connecting to an inner marker lumen of the dilator 610. The inner marker lumen of the dilator 610 may extend proximally along a length of the dilator 610 to an aperture 613. The aperture 613 may likewise be defined through at least a portion of a thickness of the dilator 610 and may connect to or otherwise communicate with the inner marker lumen (not shown).

The marker port 612, the aperture 613, and the inner marker lumen may be configured to provide a pulsatile mark defining a flow of blood FB external to the body lumen 602. The pulsatile mark indicates to a practitioner that the dilator 610 and/or the sheath 605 have been properly inserted into the body lumen 602. In embodiments, the sheath 605 and the dilator 610 are provided and inserted into the access track 604 together, while in embodiments the sheath 605 is inserted first and the dilator 610 is inserted through the inner lumen of the sheath 605 after the sheath 605 has been positioned as desired in the access track 604.

The dilator 610 may have a configuration from the distal end 611 to the proximally arranged handle portion 615 that dilates a size of the sheath 605. In embodiments, a diameter of the dilator 610 may increase substantially continuously from the distal end 611 toward the handle portion 615, or the diameter of the dilator 610 may be such that the distal end 607 only of the sheath 605 is expanded when the dilator 610 is fully inserted.

Figure 17:
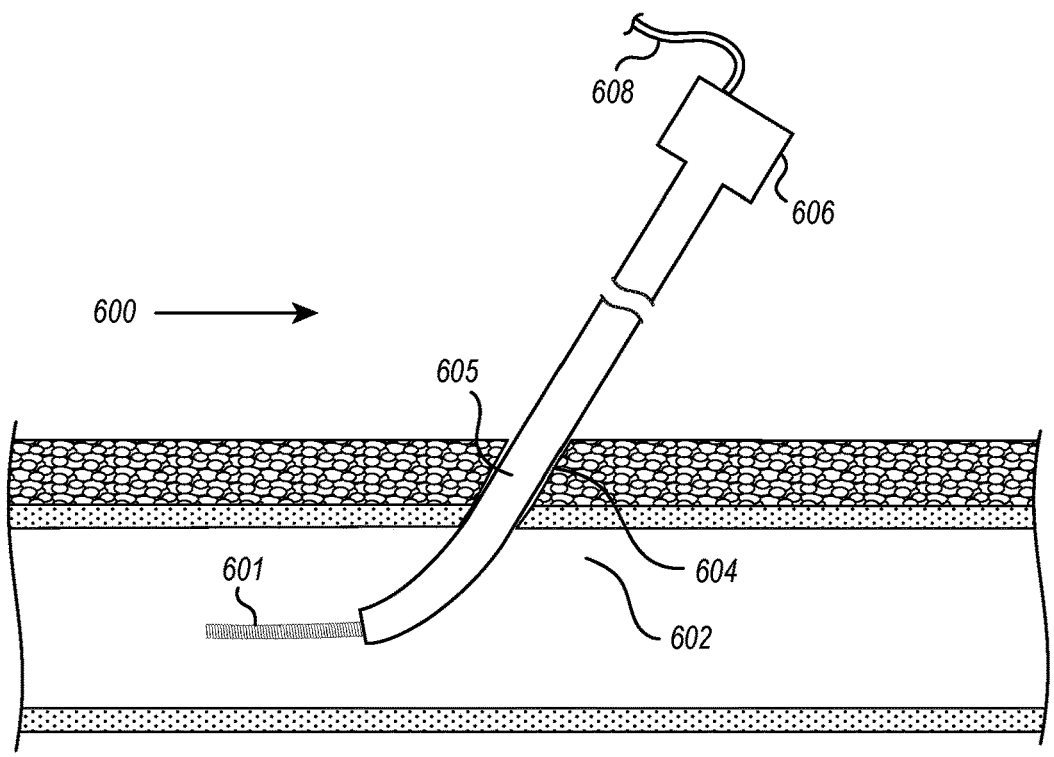
Figure 18:
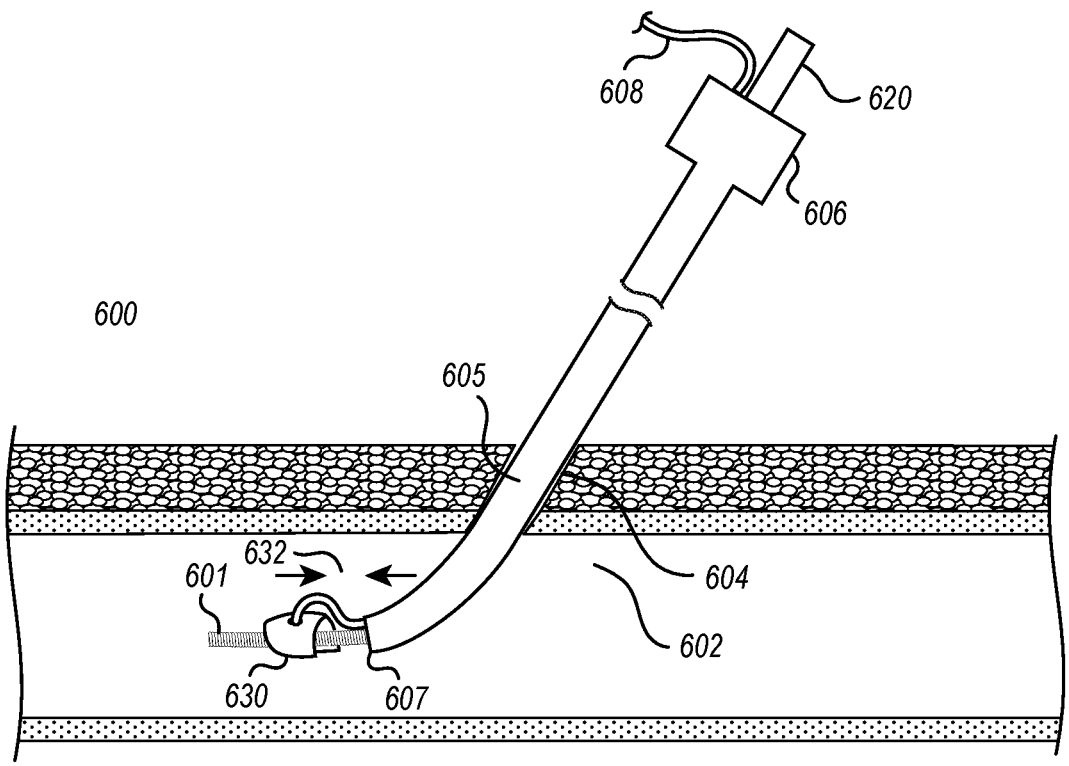

The dilator 610 may be removed from the sheath 605 proximally in a direction D16, leaving the sheath 605, the suture 608, and the guidewire 601 situated in the access track 604 and extending into the body lumen 602 as seen in FIG. 17. A delivery tube 620 may then be inserted into the inner lumen of the sheath 605 in a direction D18 as seen in FIG. 18 to eject an implant 630 from the inner lumen of the sheath 605 and into the body lumen 602.

The delivery tube 620 may be configured substantially elongate and with a diameter so as to extend into the inner lumen of the sheath 605. A distal end (not shown) of the delivery tube 620 may be shaped and configured to eject the implant 630 in a desired configuration. The delivery tube 620, as with the sheath 605 and/or the dilator 610, may be formed of any suitable material, and may have a desired degree of flexibility and/or a desired degree of strength. The properties of the delivery tube 620 may allow the delivery tube 620 to extend through a shape of the inner lumen of the sheath 605 while providing sufficient strength to be manipulated accurately by a practitioner.

The implant 630 may be a deployable foot, seal, or anchor, having a shape and material that facilitates insertion of the implant 630 through the sheath 605 and into the body lumen 602, and/or being inserted within the access track 604 so as to provide hemostasis. The implant 630 may be formed of a biocompatible material. In embodiments, the implant 630 is formed from a bioabsorbable, biodegradable, or bioresorbable material, such one or a combination of PGA, PLLA, PCL, PDLLA, PTMC, PPDO, or any other suitable material.

The implant 630 may define an attachment point whereat the suture 608 attaches to the implant 630. The suture 608 may define a knot, cleat, or other appropriate structure at the attachment point to secure the suture 608 to the implant 630. As seen in at least FIG. 18, the implant 630 may have sufficient flexibility to be provided in the sheath 605 and ejected therefrom in a folded configuration. The folded configuration may conform, for example, to a shape and size of the inner lumen of the sheath 605.

The delivery tube 620 may be configured to extend through the inner lumen of the sheath 605 by a predefined distance such that the implant 630, when ejected from the inner lumen of the sheath 605 and into the body lumen 602, extends a distance 632 distally from the distal end 607 of the sheath 605. In embodiments, the inner lumen of the sheath 605 may define a detent or mechanical stop that prevents insertion of the ejection tube 620 past a point corresponding to the distance 632. In other embodiments, the ejection tube 620 may define a structure that arrests insertion of the ejection tube 620 into the sheath 605 at a distance corresponding to or resulting in the distance 632.

Figure 19:
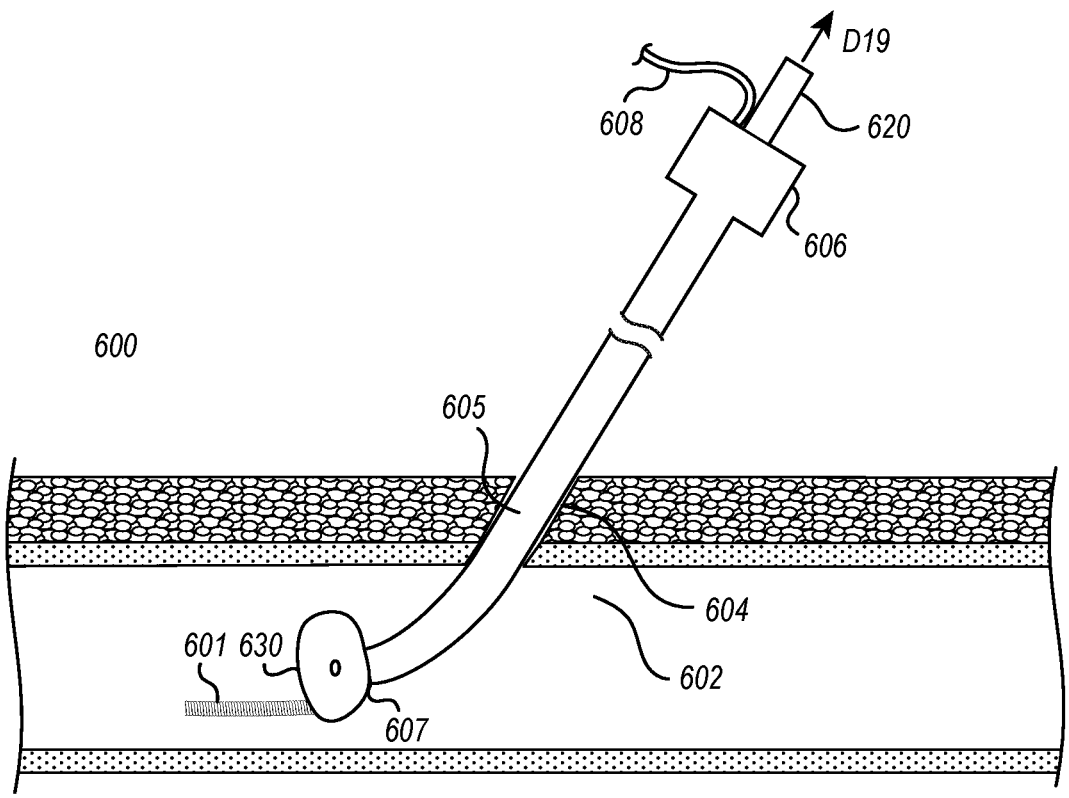

After the implant 630 has been ejected into the body lumen 602, tension may be applied to the suture 608 in a direction D19 by a practitioner to close the distance 632 between the implant 630 and the distal end 607 of the sheath 605. The tension and/or contact with the distal end 607 of the sheath 605 may additionally cause the implant 630 to toggle from the folded configuration to an unfolded configuration, as shown in FIG. 19.

With the implant 630 contacting the distal end 607 of the sheath 605, the sheath 605 may be retracted distally in a direction D20 by the practitioner outwardly through the access track 604. The sheath 605 may be withdrawn until the vessel wall 603 is located. This may be accomplished when the practitioner detects, for example, resistance provided by the implant 630, in the unfolded configuration, contacting a surface of the vessel wall 603 proximate the access track 604.

The tension applied to the suture 608 may be maintained while the sheath 605 is withdrawn to ensure that the implant 630 and the distal end 607 of the sheath 605 remain in contact during the withdrawal process. This also advantageously ensures that the implant 630 is applied against the vessel wall 603 with a desired degree of force such that hemostasis is achieved.

Figure 21:
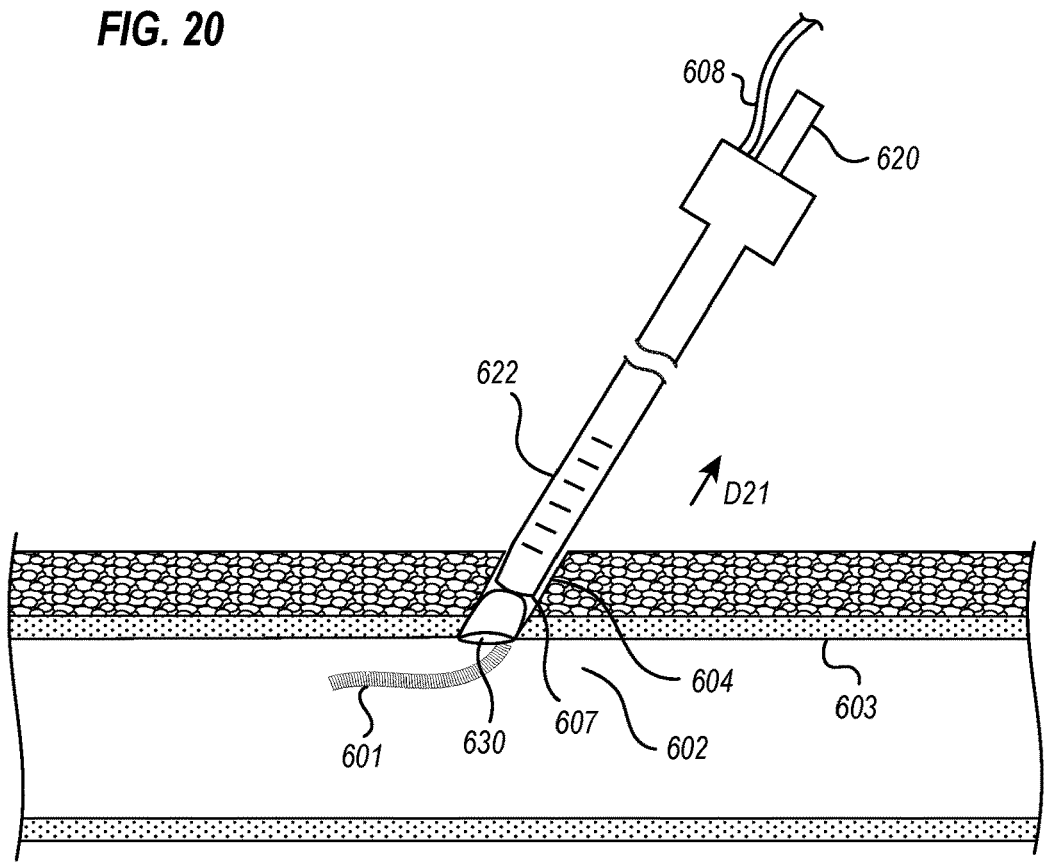

The sheath 605 may be further withdrawn by a desired or predetermined further distance. The predetermined distance may be indicated to a practitioner by one or more indicia 622 on an external surface of the sheath 605 as seen in FIG. 21. When the vessel wall 603 has been located, the practitioner may note the current location of the sheath (e.g. by an index line of the sheath corresponding to the surface of the skin) and proceed to retract the sheath to a next index line.

This advantageously allows the practitioner to withdraw the implant a desired distance within the access track 604. The indicia 622 may be index lines spaced apart by the further distance, such that upon locating the vessel wall 603, the practitioner may note the current location and simply withdraw the sheath 605 by the distance between adjacent index lines.

As seen in FIG. 21, the sheath 605 may be withdrawn a further distance through the access track 604, resulting in the implant 630, a portion of which may remain positioned at the vessel wall 603, extending partly into the access track 604 to an implant configuration. The further distance may conveniently be a distance corresponding to one or more of the indicia 622. The implant configuration may be a folded configuration in which a surface of the implant 630 remains at the vessel wall 603 and/or flush therewith, while a remainder of the implant 630 extends within the access track 604, preventing blood flow from the body lumen 602 into the access track 604.

Further regarding FIG. 21, the implant configuration may define a substantially conical or semi-circular shape. The implant 630 may thereby be flush with the vessel wall 603 while extending a distance into the access track 604 sufficient to prevent blood flow around the implant 630. Once hemostasis has been confirmed, the guidewire 601 may be retracted from the body lumen 602 through the inner lumen of the sheath 605.

Figure 22:
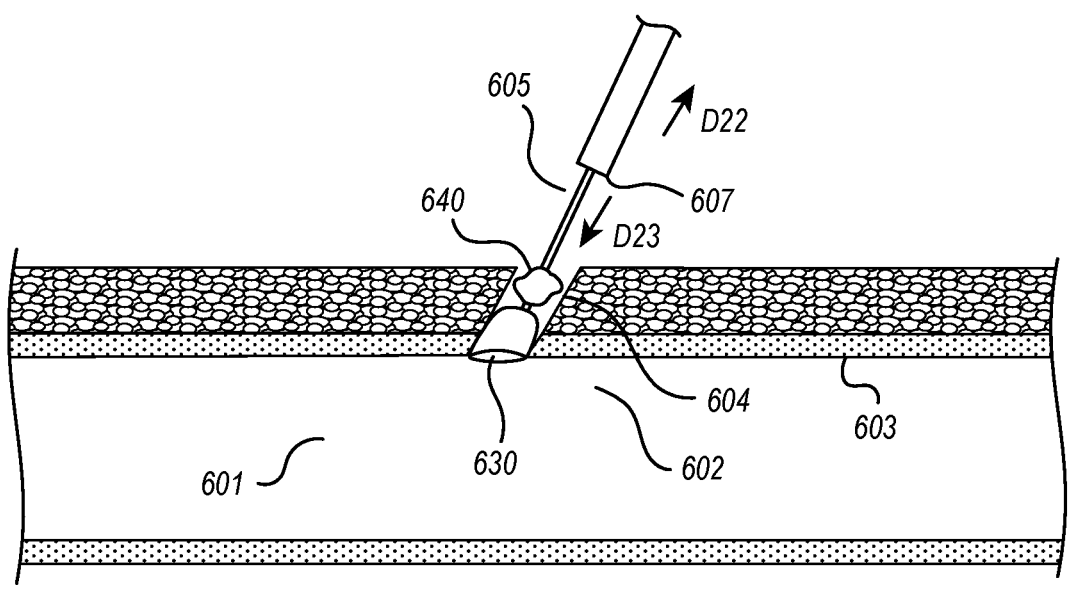

With the implant 630 in the implant configuration shown in FIG. 21, the sheath 605 may be fully retracted from the access track 604 in a direction D22 as shown in FIG. 22, leaving the implant 630 in position in the access track 604. The suture 608, extending through the inner lumen of the sheath 605, may be configured to deliver a sealant 640 into the access track 604 in a direction D23 and proximate the implant 630.

The sealant 640 may be any suitable sealant, including, for example, a solid, preformed cylinder or other solid mass that is configured to be pushed into place over the suture 608. The solid sealant may include one or more of polyethylene glycol (PEG), hyaluronic acid, gelatin, and collagen. As the sealant 640 is positioned within the access track, the sealant 640 absorbs fluid and swells, thereby sealing the access track 604 and effecting hemostasis.

While a solid sealant 640 has been shown and described, it will be appreciated that the access closure device 600 may cooperate with a liquid sealant, for example a sealant solution configured to provide hemostasis in cooperation with the implant 630.

The implant 630 may advantageously be a compliant or semi-compliant implant and formed of bioabsorbable, biodegradable, or bioresorbable materials such that the problem of arterial plaque being displaced by an anchor or implant is addressed and mitigated.

Figure 23:
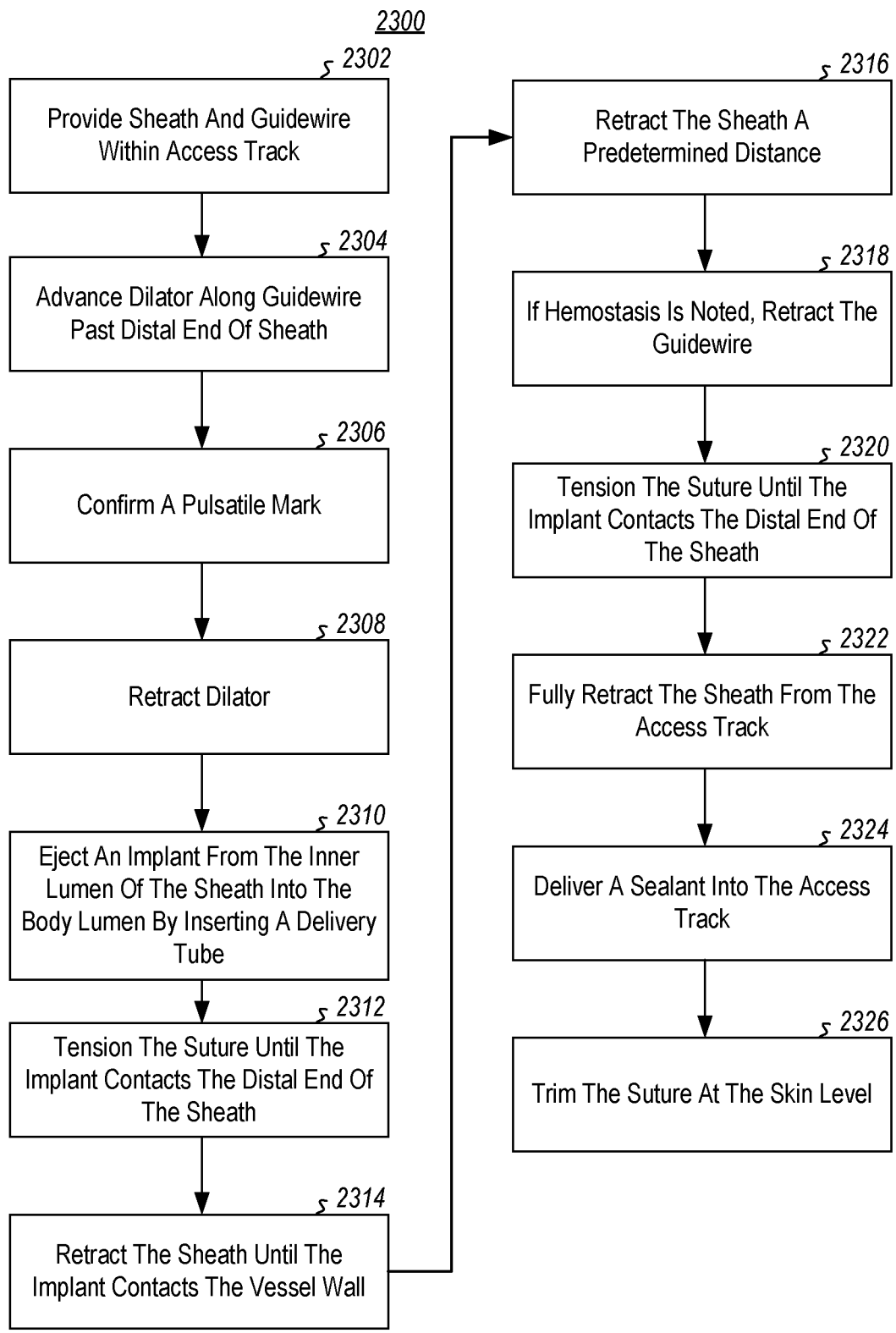
FIG. 23 illustrates a method of using an access closure device according to the embodiment of FIGS. 16-22.
Figure 24A:
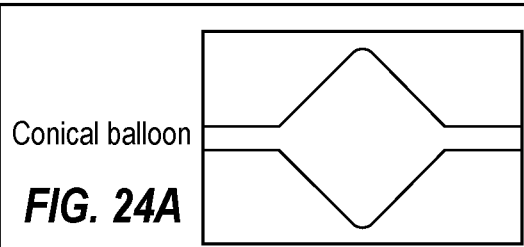
FIGS. 24A-24L illustrates various balloon configurations of the balloon delivery system according to the present invention, including but not limited to the embodiments of FIGS. 1-15B.
Figure 24B:
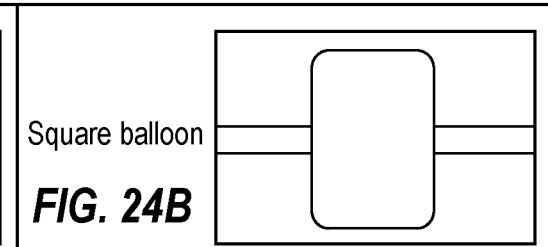
Figure 24C:
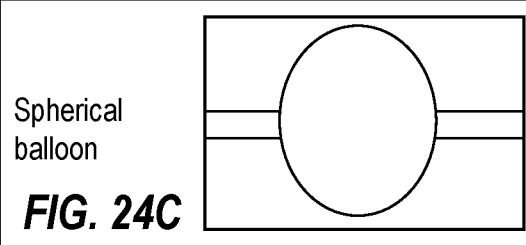
Figure 24D:
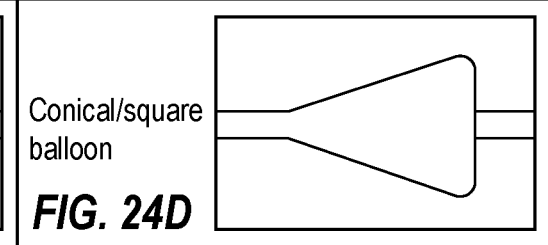
Figure 24E:
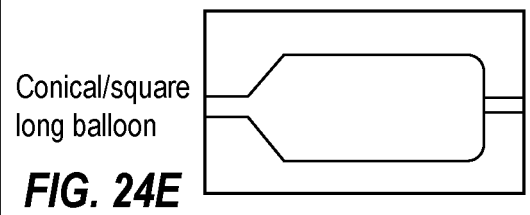
Figure 24F:
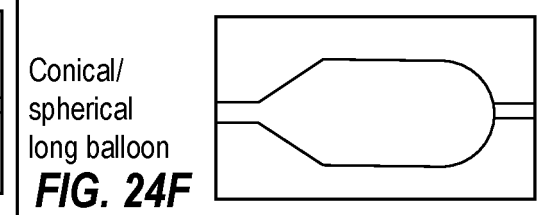
Figure 24G:
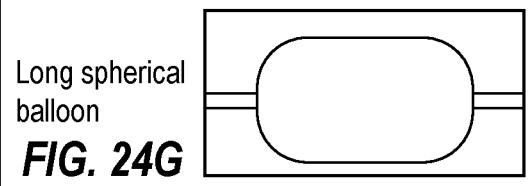
Figure 24H:
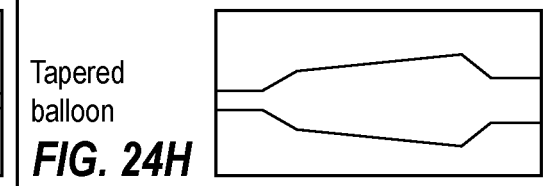
Figure 24I:
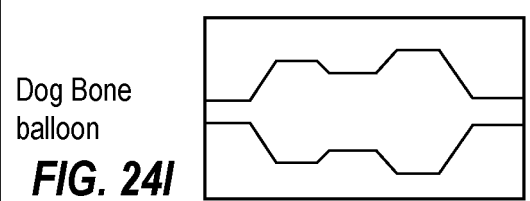
Figure 24J:
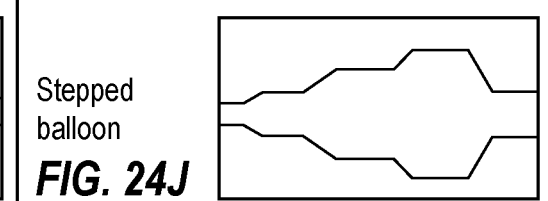
Figure 24K:
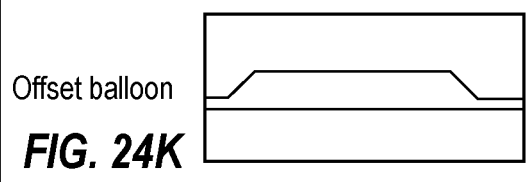
Figure 24L:
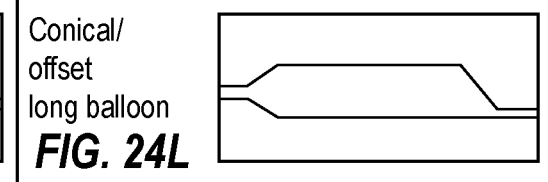

FIG. 23 shows an exemplary method for closing an access track or orifice. The exemplary method 2300 includes one or more of the following steps, not necessarily in the following order. The method 2300 includes a first step 2302 of providing an access closure device comprising, for instance, a sheath, a suture, an implant secured to the suture, and a guidewire within an access track of a body lumen, as shown and described regarding FIG. 16. The access closure device may be an over-the-wire system facilitating accurate and convenient access to the access track and the body lumen.

Figure 16:
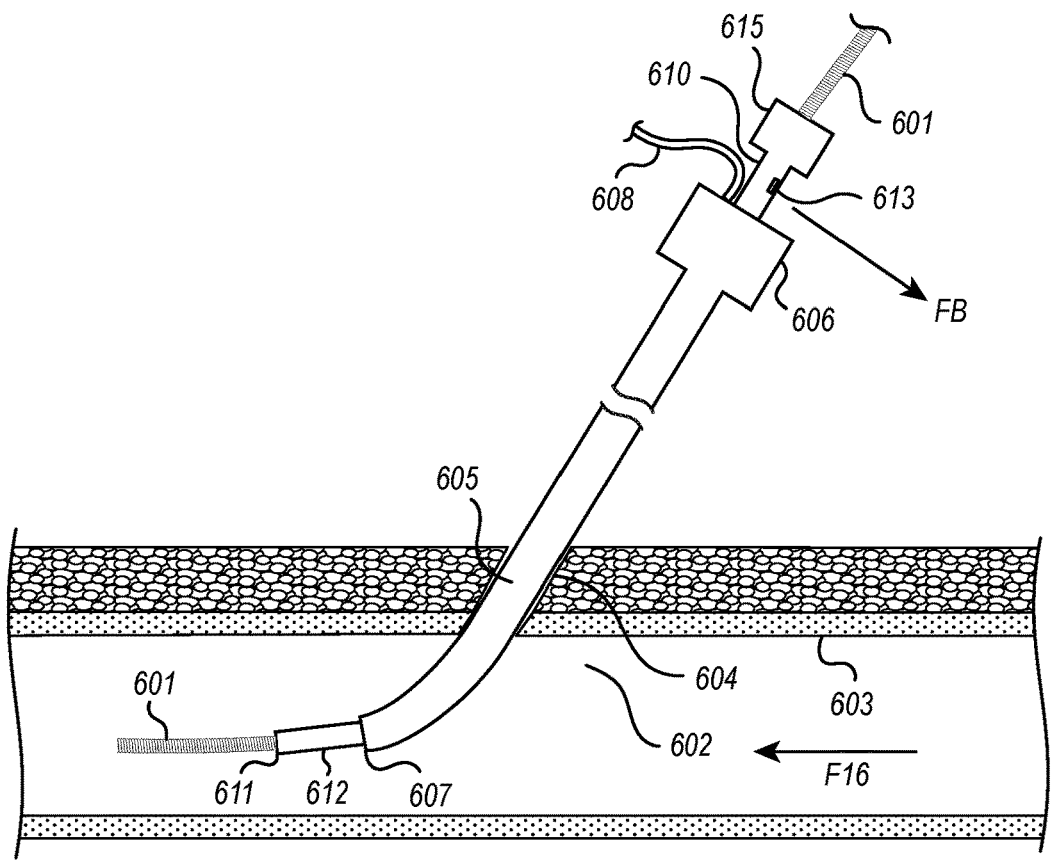
FIGS. 16-22 illustrate the use of an access closure device according to another embodiment of the present invention.

The method 2300 may include a second step 2304 of advancing a dilator along the guidewire through the inner lumen of the sheath, past a distal end of the sheath, and into the body lumen as also shown and described regarding FIG. 16. The dilator may extend through an inner lumen of the sheath and conform to a shape of the sheath within the access track and the body lumen.

The method 2300 may also include a third step 2306 of confirming a pulsatile mark as also shown regarding FIG. 16. The pulsatile mark may be determined by a flow of blood through an aperture defined through a thickness of the dilator proximate the proximal end of the dilator and in communication with an aperture defined through a thickness of the dilator proximate a distal end of the dilator within the body lumen. The pulsatile mark may indicate to a practitioner that the dilator is properly positioned within the body lumen and relative to the sheath. The apertures of the dilator may advantageously provide a blood mark regardless of an access position of the access closure device.

A fourth step 2308 includes retracting the dilator from the sheath and outwardly from the access track as shown and described regarding FIG. 17. Though the dilator may be removed, the guidewire, the suture, and the implant may remain arranged within the inner lumen of the sheath.

After the retraction of the dilator in the fourth step 2308, the method 2300 includes a fifth step 2310 of ejecting the implant from the inner lumen of the sheath into the body lumen by inserting a delivery tube into the inner lumen of the sheath, as shown and described regarding FIG. 18. The delivery tube may be configured in size and shape to be inserted into the inner lumen of the sheath and/or to follow the shape of the sheath within the body lumen and the access track. The delivery tube may be configured to eject or push the implant outwardly from the inner lumen of the sheath by a distance.

The implant may be attached to the suture by a knotted, cleated, other suitable connection at a suture attachment point. The implant, the suture, or both may be formed from one or more bioabsorbable, biodegradable, or bioresorbable materials, such as bioabsorbable, biodegradable, or bioresorbable polymers and may have desired strength, stiffness, and absorption, resorption, or degradation rate. The implant may be configured to be compliant or semi-compliant so as to be drawn a desired degree proximate and/or into the access track, as well as to be provided in the sheath in a folded configuration and to extend to an unfolded configuration in the body lumen.

A sixth step 2312 includes tensioning the suture in a proximal direction relative to the sheath such that the implant contacts the distal end of the sheath. The implant may be expanded from a folded configuration suitable for conforming to the inner lumen of the sheath to an unfolded configuration suitable for implanting at the vessel wall about the access track to provide hemostasis.

Figure 20:
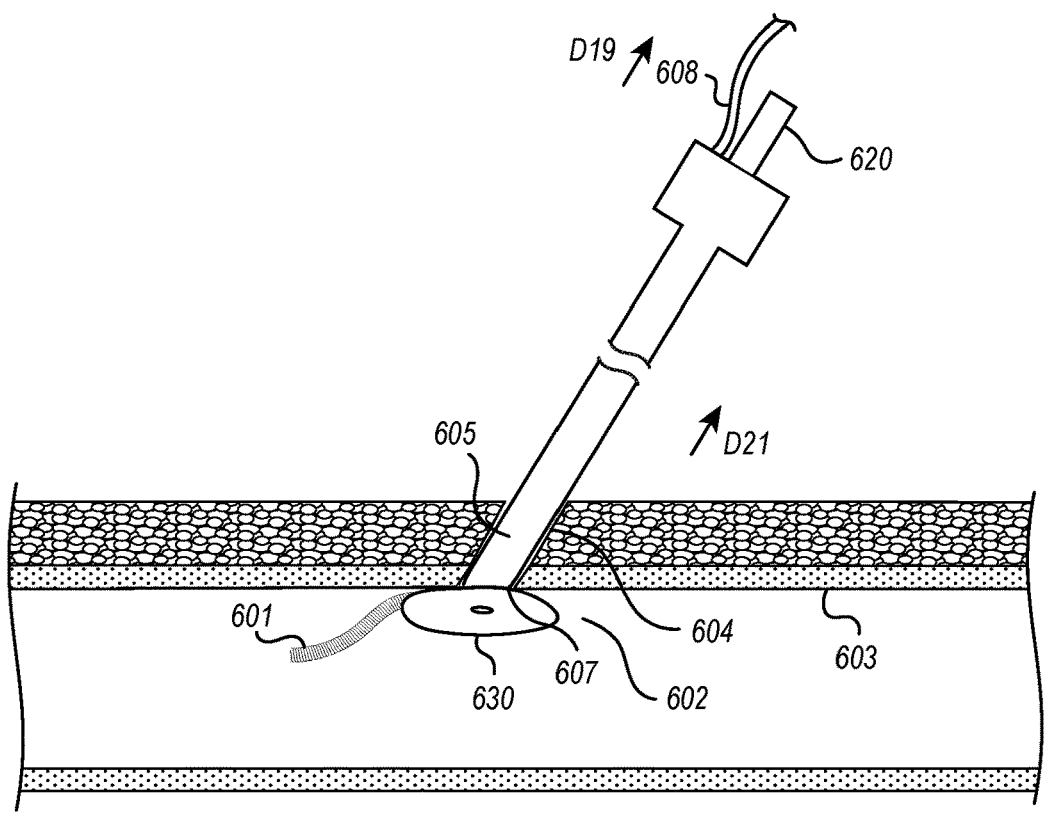

A seventh step 2314 includes retracting the sheath proximally until the implant contacts the vessel wall, with the suture still under tension, as shown and described regarding FIG. 20. This advantageously allows the practitioner to ensure that the implant is precisely arranged at a desired location at the access track.

An eighth step 2316 includes further retracting the sheath a predetermined distance proximally through the access track. The distance may be predetermined and may be shown as one or more indicia on an exterior surface of the sheath. The step 2316 may include the practitioner identifying a current location of the sheath relative to the access track based on a first indicium, and withdrawing the sheath by a predetermined distance corresponding to a distance between the first indicium and another indicium. The distance may be predetermined and configured to ensure that the implant under tension is applied against the vessel wall with a desired degree of force.

After the eighth step 2316, a ninth step 2318 may include retracting the guidewire from the body lumen through the inner lumen of the sheath if hemostasis is noted. Hemostasis may be noted by the practitioner based on an amount of blood flow through the access track after the sheath has been withdrawn by the distance.

A tenth step 2320 may include tensioning the suture until the implant contacts the distal end of the sheath within the access track as shown and described regarding FIG. 21. The implant may be configured to be drawn inwardly into the access track under the tension from the suture with a surface of the implant remaining at or proximate the vessel wall such that a portion of the implant is substantially flush with a surface of the vessel wall.

Once the implant has been tensioned in the tenth step 2320, the sheath, in which the delivery tube may still be positioned, may be fully retracted from the access track in an eleventh step 2322, with the suture and the implant remaining in place in the access track.

In a twelfth step 2324, a sealant is delivered into the access track along the suture as shown and described regarding FIG. 22. The sealant may be a solid sealant material and arranged around the suture so as to be slidably delivered into the access track. The sealant may be delivered into the access track proximate the implant so as to absorb fluids and ensure hemostasis. The sealant may be configured to expand upon absorption of fluids to fill the access track. The sealant may also take the form of a fluid, such as a gel.

In a thirteenth step 2326, any remaining components of the closure system are removed from the access track and the suture is trimmed at the skin level and the access track is finally sealed. Because of the advantageous cooperation of the implant and the sealant, hemostasis is ensured without manual compression, with high accuracy and convenience for a practitioner, and with fewer steps than are required in existing access closure modalities and systems.

While distinct balloon delivery system and sealant delivery systems and components for use therewith, as well as implant devices and sealant materials and components for use therewith, have been described regarding an access closure device, it will be appreciated that the balloon delivery system and the sealant delivery system may be integrated in a single delivery shaft, the integrated delivery shaft configured to deliver a balloon segment, a balloon, a suture, a snare wire, and/or sealant to a body lumen and access track as described above.

By providing an access closure device according to the disclosed embodiments, the problem of existing vessel closure devices and approaches being poorly adapted to providing efficient and effective hemostasis without manual compression is addressed. The access closure device advantageously provides a balloon delivery system for inflating and positioning a bioabsorbable, biodegradable, or bioresorbable balloon at an access track to provide hemostasis and to provide a sealant proximate the balloon in the access track to further effect hemostasis and cooperate with the balloon without having the deflate and remove the balloon through the access track after or while providing the sealant. The access closure device is deployable through a procedural sheath and facilitates a practitioner fully verifying hemostasis before removing the procedural sheath.

The closure device discussed with the various example embodiments of the present invention may include various other configurations. For example, any configuration of the closure device that includes a closure element that is able to anchor within the tissue track and apply pressure to the outside surface of the body lumen wall may be used with the closure device contemplated with the present invention.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements. As used in the description above the terms "distal" and "proximal" are provided as indications of the relative location or orientation of a component or structure in relation to the physician or operator.

Following are some further example embodiments of the invention. These are presented only by way of example and are not intended to limit the scope of the invention in any way. Further, any example embodiment can be combined with one or more of the example embodiments.

Embodiment 1. An access closure device including a balloon delivery system. The delivery system includes a balloon, a balloon segment, at least one valve, and an attachment portion. The balloon segment, configured to support the balloon, has a lumen and a plurality of openings in fluid communication with an interior of the balloon and the lumen. The at least one valve is configured to selectively seal the lumen of the balloon segment. The attachment portion, proximate the at least one valve, is configured to releasably couple the balloon segment to a portion of the balloon delivery system.

Embodiment 2: The access closure device of embodiment 1, wherein the balloon delivery system comprises a delivery shaft configured to releasably couple to the attachment portion of the balloon segment.

Embodiment 3: The access closure device of any of the embodiments 1-2, wherein the delivery shaft includes at least one weeping port proximate the balloon segment and in fluid communication with a corresponding check valve.

Embodiment 4: The access closure device of any of the embodiments 1-3, wherein the at least one weeping port is configured to open upon the balloon exceeding a predetermined pressure threshold, the at least one weeping port opening to an exterior of the delivery shaft.

Embodiment 5: The access closure device of any of the embodiments 1-4, wherein the balloon delivery system is provided with an integrated delivery shaft.

Embodiment 6: The access closure device of any of the embodiments 1-5, wherein the balloon and the balloon segment comprise bioabsorbable, biodegradable, or bioresorbable material.

Embodiment 7: The access closure device of any of the embodiments 1-6, further including a sealant delivery system including a sealant delivery shaft configured to deliver a sealant to an access track.

Embodiment 8: The access closure device of any of the embodiments 1-7, wherein the sealant delivery shaft defines a lumen and corresponding ejection shaft, the ejection shaft slidingly engaged with the lumen of the sealant delivery shaft.

Embodiment 9: The access closure device of any of the embodiments 1-8, wherein the sealant is provided as a liquid sealing solution including one or a combination of polyethylene glycol, polyethylene oxide, hyaluronic acid, gelatin, or collagen.

Embodiment 10: The access closure device of any of the embodiment 9, wherein the liquid sealing solution is a two-part system premixed prior to administration through the sealant delivery system.

Embodiment 11: The access closure device of any of the embodiments 9-10, wherein the liquid sealing solution includes at least one gelling or cross-linking mechanism.

Embodiment 12: The access closure device of any of the embodiments 7-11, wherein the sealant is provided as a solid structure including crosslinked polyethylene glycol, polyethylene oxide, hyaluronic acid, gelatin, or collagen.

Embodiment 13: The access closure device of any of the embodiments 2-12, wherein the delivery shaft defines at least one indicium on an outer surface of the delivery shaft.

Embodiment 14: The access closure device of any of the embodiments 2-13, wherein a syringe is in fluid communication with the lumen of the delivery shaft.

Embodiment 15: A method for closing an access track, the method including the steps of providing a procedural sheath through the access track in a body lumen, advancing a balloon delivery system comprising a balloon and a balloon segment releasably attached to a delivery shaft into a lumen of the procedural sheath and into the body lumen, partially inflating the balloon of the balloon delivery system, retracting the balloon delivery system until the balloon contacts a distal tip of the procedural shaft, and retracting the balloon delivery system and the procedural sheath outwardly from the body lumen through the access track until the balloon contacts an inner wall of the body lumen such that resistance to further retraction is generated.

Embodiment 16: The method for closing an access track of embodiment 15, further including the steps of retracting the procedural sheath a distance to align with at least one indicium defined on an outer surface of the delivery shaft, and tensioning at least one suture, the suture connected to the balloon and/or the balloon segment, such that the balloon is retracted a distance into the access track.

Embodiment 17: The method for closing an access track of embodiment 16, the method further including the steps of advancing a bypass tube distally on the delivery shaft, fully inflating the balloon, and detaching the balloon and the balloon segment from the balloon delivery system.

Embodiment 18: The method for closing an access track of any of embodiments 16-17, the method further comprising the steps of removing the procedural sheath and the delivery system from the access track, snaring the at least one suture using a snare wire of a sealant delivery system, advancing at least one sealing component into the access track, cutting and sealing the at least one suture in the access track, and attaching the at least one suture to a skin surface using a cover.

Embodiment 19: The method for closing an access tracked of any of embodiments 16-17, the method using any of the access closure devices of embodiments of any of claims 1-14.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. It shall be further understood that although the present invention has been described in relation to vessel closure, it is contemplated that the closure component of the present invention may be utilized to close other openings in the body such as patent foramen ovale (PFO) openings, or openings formed in organs such as the stomach for certain surgical procedures.

What is claimed is:

1. An access closure device comprising:
   a balloon delivery system comprising:
      a balloon;
      a balloon segment supporting the balloon, the balloon segment having a lumen and a plurality of openings in fluid communication with an interior of the balloon and the lumen;
      at least one valve selectively sealing the lumen of the balloon segment;
      an extension portion proximate the at least one valve, the extension portion configured to releasably couple the balloon segment to a portion of the balloon delivery system; and
      a delivery shaft configured to releasably couple to the extension portion the delivery shaft and the extension portion each being formed of materials having a coefficient of friction, wherein when a first force is configured to be exerted in a direction transverse to a longitudinal axis of the delivery shaft by a tissue tract through which the balloon delivery system passes, contact is configured to be maintained between the extension portion and the delivery shaft,
   wherein, once inflated within a body lumen, the balloon is configured to remain inside at least a portion of the body lumen.

2. The access closure device of claim 1, wherein the balloon delivery system is provided with an integrated delivery shaft.

3. The access closure device of claim 1, wherein the delivery shaft defines at least one indicium on an outer surface of the delivery shaft.

4. The access closure device of claim 1, wherein a syringe is in fluid communication with the lumen of the delivery shaft.

5. The access closure device of claim 1, wherein the balloon and the balloon segment comprise a bioabsorbable, biodegradable, or bioresorbable material.

6. The access closure device of claim 1, further comprising a sealant delivery system comprising a sealant delivery shaft configured to deliver a sealant to an access track.

7. The access closure device of claim 6, wherein the sealant delivery shaft defines a lumen and corresponding ejection shaft, the ejection shaft slidingly engaged with the lumen of the sealant delivery shaft.

8. The access closure device of claim 6, wherein the sealant is provided as a liquid sealing solution comprising one or a combination of polyethylene glycol, polyethylene oxide, hyaluronic acid, gelatin, or collagen.

9. The access closure device of claim 8, wherein the liquid sealing solution is a two-part system premixed prior to administration through the sealant delivery system.

10. The access closure device of claim 9, wherein the liquid sealing solution comprises at least one gelling or cross-linking mechanism.

11. The access closure device of claim 6, wherein the sealant is provided as a solid structure comprising cross-linked polyethylene glycol, polyethylene oxide, hyaluronic acid, gelatin, or collagen.

12. A method for closing an access track, the method comprising the steps of:
   providing a procedural sheath through the access track, through an opening in a wall of a body lumen, and into the body lumen;
   advancing a balloon delivery system comprising a balloon and a balloon segment releasably attached to a delivery shaft into a lumen of the procedural sheath and into the body lumen;
   partially inflating the balloon of the balloon delivery system;
   retracting the balloon delivery system until the balloon is in contact with a distal tip of the procedural shaft;
   retracting the balloon delivery system and the procedural sheath outwardly from the body lumen through the opening in the wall of the body lumen and into the access track until the partially inflated balloon contacts an inner wall of the access track and the wall of the body lumen such that resistance to further retraction is generated; and
   detaching the balloon and the balloon segment from the balloon delivery system and withdrawing a reminder of the balloon delivery system while leaving the balloon and balloon segment within at least a portion of the body lumen, the opening in the wall of the body lumen, and the access track to close the access track and the opening in the wall of the body lumen.

13. The method for closing an access track of claim 12, the method further comprising the steps of:
   retracting the procedural sheath a distance to align with at least one indicium defined on an outer surface of the delivery shaft; and
   tensioning at least one suture, the suture connected to the balloon and/or the balloon segment, such that the balloon is retracted a distance into the access track.

14. The method for closing an access track of claim 13, the method further comprising the steps of:
   advancing a bypass tube distally on the delivery shaft;
   fully inflating the balloon.

15. The method for closing an access track of claim 13, the method further comprising the steps of:
   removing the procedural sheath and the delivery system from the access track;
   snaring the at least one suture using a snare wire of a sealant delivery system;
   advancing at least one sealing component into the access track;
   cutting and sealing the at least one suture in the access track;
   attaching the at least one suture to a skin surface using a cover.

* * * * *